(12) United States Patent
Breitenbach et al.

(10) Patent No.: US 7,919,117 B2
(45) Date of Patent: Apr. 5, 2011

(54) TRANSDERMAL DELIVERY OF (R)-3,3-DIPHENYLPROPYLAMIN-MONOESTERN

(75) Inventors: Armin Breitenbach, Monheim (DE); Claus Meese, Monheim (DE); Hans-Michael Wolff, Monheim (DE); Roland Drews, Monheim (DE)

(73) Assignee: UCB Pharma GmbH, Monheim (DE)

( * ) Notice: Subject to any disclaimer, the term of this patent is extended or adjusted under 35 U.S.C. 154(b) by 0 days.

(21) Appl. No.: 12/417,405

(22) Filed: Apr. 2, 2009

(65) Prior Publication Data

US 2009/0274761 A1 Nov. 5, 2009

Related U.S. Application Data

(62) Division of application No. 10/533,683, filed as application No. PCT/EP2004/003574 on Apr. 3, 2004, now Pat. No. 7,670,621.

(30) Foreign Application Priority Data

Apr. 8, 2003 (DE) .................................. 103 15 878

(51) Int. Cl.
*A61K 9/14* (2006.01)
(52) U.S. Cl. ........................................ 424/484; 514/546
(58) Field of Classification Search .................. None
See application file for complete search history.

(56) References Cited

U.S. PATENT DOCUMENTS

| | | | |
|---|---|---|---|
| 4,675,009 A | 6/1987 | Hymes et al. | |
| 5,271,940 A | 12/1993 | Cleary et al. | |
| 6,425,892 B2 | 7/2002 | Southam et al. | |
| 6,555,129 B1 | 4/2003 | Arth et al. | |
| 6,638,528 B1 | 10/2003 | Kanios | |
| 6,743,441 B2 | 6/2004 | Sanders et al. | |
| 6,858,650 B1 * | 2/2005 | Meese ........................... | 514/530 |
| 6,893,655 B2 | 5/2005 | Flanigan et al. | |
| 7,230,030 B2 | 6/2007 | Meese et al. | |
| 7,246,486 B2 | 7/2007 | Nakagawa et al. | |
| 2003/0157156 A1 | 8/2003 | Hsu et al. | |
| 2004/0081683 A1 | 4/2004 | Schacht et al. | |

FOREIGN PATENT DOCUMENTS

| | | |
|---|---|---|
| EP | 0957073 | 11/1999 |
| RU | 2199525 | 2/2003 |
| WO | 93/23025 | 11/1993 |
| WO | 99/58478 | 11/1999 |
| WO | 01/35957 | 5/2001 |
| WO | 2004/089872 | 10/2004 |

* cited by examiner

*Primary Examiner* — Daniel M Sullivan
*Assistant Examiner* — Chukwuma O Nwaonicha
(74) *Attorney, Agent, or Firm* — Kenyon & Kenyon LLP

(57) ABSTRACT

The invention relates to a device for transdermally administering a compound of formula (I), wherein A represents hydrogen or deuterium, R represents a group selected among $C_{1-4}$alkyl, $C_{3-10}$cycloalkyl, or phenyl, each of which can be substituted by $C_{1-3}$alkoxy, fluoride, chlorine, bromine, iodine, nitro, amino, hydroxy, oxo, mercapto, or deuterium, the C atom marked by * (asterisk) being provided in the R configuration. The invention is characterized in that the compound of general formula (I) is provided in a polymer matrix and is released at a dose of 0.5 to 20 mg per day through human skin. The invention further relates to the use of said compounds of formula (I) for producing transdermal medicaments.

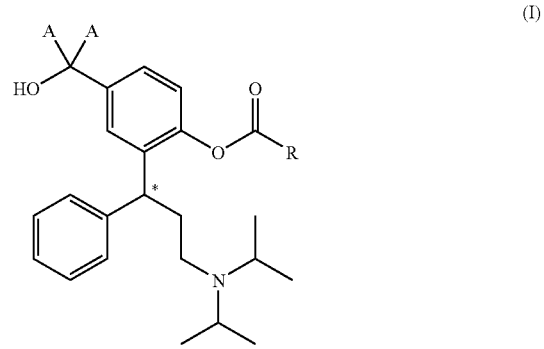

(I)

24 Claims, 5 Drawing Sheets

Diagrammatic Composition of a Monolithic TTS

TRANSDERMAL DELIVERY OF (R)-3,3-DIPHENYLPROPYLAMIN-MONOESTERN

CROSS-REFERENCE TO RELATED APPLICATIONS

This application is a divisional of U.S. patent application Ser. No. 10/533,683, filed Apr. 26, 2005, which is a 371 of International Patent Application No. PCT/EP2004/003574, filed Apr. 3, 2004, which claims priority to German Patent Application No. 10315878.2, filed Apr. 8, 2003. Each of the above referenced applications is hereby incorporated herein in its entirety.

BACKGROUND OF THE INVENTION

The invention concerns a medicine for the transdermal delivery of (R)-3,3-diphenylpropylamine-monoesters as well as their application for the manufacture of a medicine for transdermal delivery.

The proportion of seniors within the total population has gone up significantly in the past 50 years. Bladder dysfunctions belong to the most common geriatric diseases in this group. Therefore, ever greater and more specific significance is being attached to the development of a most effective and gentle treatment of bladder complaints.

In the case of urge incontinence the dysfunction lies in a malfunction of the bladder muscle. Frequently the cause is a stimulation or more precisely a hyperactivity of the muscarinic receptors. For this reason use of the antimuscarinic active ingredients Tolterodin and Oxybutynin is preferred for the treatment of the hyperactive bladder and the associated symptoms such as increased urinary urgency, abnormally frequent micturation or nocturia.

However, Oxybutynin is an effective antimuscarinic active ingredient that has serious side effects. Notably the pronounced dryness of the mouth is felt by many patients to be extremely unpleasant.

By comparison with Oxybutynin Tolterodin appears to exhibit lower rates of muscarinic side effects. In an organism Tolterodin is predominantly dealkylated into active main metabolites 2-[3-(1,1-diisopropylamino)-1-phenylpropyl]-4-(hydroxy methyl)phenol by the cytochrome P450-isoenzyme 2D6 as well as—slowly—into inactive metabolites by the cytochrome P 450 isoenzyme 3A4.

Since Tolterodin is metabolized exclusively by the P450-isoenzyme, there is the potential danger of interactions with the breakdown of other active ingredients, for example, with Warfarin (Colucci, Annals of Pharmacotherapy 33, 1999, 1173), antimycotics such as Ketoconazol (Brynne, Br J Clin Pharmacol 48, 1999, 564) macrolide antibiotics or protease inhibitors. This danger is present particularly in the case of the so-called slow metabolizers, which have a lack of 2D6, metabolize Tolterodin exclusively through 3A4 and exhibit a distinctly increased Tolterodin concentration in plasma.

WO 99/58 478 describes new derivates of 3,3-diphenyl-propylamines as active muscarinic ingredients. The disclosed 3,3-diphenylpropylamine-derivates are prodrugs from 2-[3-(1,1-diisopropylamino)-1-phenylpropyl]-4-(hydroxy methyl)phenol and are hydrolyzed by esterases upon entering through biological membranes as well as in plasma. For this reason the 2D6-dependent degradation device does not apply.

In contradistinction to Tolterodin such 3,3-diphenylpropylamine derivates, for example, 2-[3-(1,1-Diisopropylamino)-1-phenylpropyl)-4-(hydroxy methyl)phenyl isobutyrate (INN: fesoterodine), therefore do not show a tendency towards accumulation even in the case of slow metabolizers, they do not interfere with P450 inductors/inhibitors and they possess an advantageous safety profile with regard to potential interactions of active ingredients and accumulation of active ingredients.

Therefore, the need arose to make the advantages of the 3,3-diphenylpropylamine derivate described in WO 99/58478, particularly the advantages of the fesoterodine, available to the collective of patients. The metabolism method of Tolterodin and the disadvantages of Oxybutynin (dry mouth) alone make clear the medical need for a medicine that does not exhibit the disadvantages of both of the previously named substances.

3,3-diphenylpropylamine monoesters may be present as stabile crystalline salts. fesoterodine-hydrogen fumarate is an example preferred for this purpose. Salts of this sort are described in WO 01/35957 and are particularly suited for oral or parenteral treatment of the hyperactive bladder.

Even though oral administration of these compounds represents an appropriate form of presentation for most patients, there is a need for an alternative form of administration. This need results not least at the old ages of the patients affected by dysfunctions of bladder motility, in which cases an array of reasons are able to speak against the oral administration of the drugs.

There is frequently a multimorbidity within this collective of patients, whereby as a general rule the patients are taking several different medications. Avoidance of passage through the intestine and the first liver passages and consequently a non-oral form of administration are frequently desirable to prevent interactions with the resorption of other drugs and/or not to burden the gastro-intestinal tract as well as the liver with additional drugs.

In addition, a number of older patients have problems with swallowing the solid forms of drugs, while other geriatric patients exhibit impaired gastrointestinal absorption, for example, as a result of acute or chronic gastrointestinal diseases or the taking of anti-infectives.

Ultimately a more constant plasma concentration of the active substance can be achieved using a form of administration that avoids the first-pass effect of the first liver passage and that also exhibits a retarding effect, which in general simultaneously leads to a lowering of the danger of undesired side effects, dryness of the mouth in particular, with unaltered or even improved clinical effectivity.

SUMMARY OF THE INVENTION

The transdermal administration of a 3,3-diphenylpropylamine-monoester and in particular of fesoterodine is an attractive option because, for instance, it avoids the peak concentrations in the plasma associated with oral administration and the danger of muscarinic side effects associated with it, notably dryness of the mouth.

If there is success in transporting the most even dose possible of the active agent into the circulatory system over a longer period of time, the total daily dose and with it the effectiveness of the active ingredient could be raised and the occurrence of undesired side effects lowered at the same time.

It was therefore an objective of this invention to provide a device or a medicine respectively for the transdermal delivery of a compound of the general Formula I which satisfies the following conditions:

1. The device should be able to administer a therapeutically effective daily dose of a 3,3-diphenylpropylamine-monoester transdermally.
2. The active ingredient should be administered in a therapeutically effective amount through the skin over a longer period of time, meaning over at least 24 hours, preferably over 48 or 72 hours following the one time application of the medicine.
3. The active ingredient should be taken in through the skin at the most constant rate possible so that a nearing constant plasma level is sustained over the scheduled duration of application.
4. The surface of the skin, which is in contact with the device (e.g. the patch) should preferably be a maximum size of 50 $cm^2$.
5. A skin penetration enhancer should be dispensed with, if possible.
6. The device should be constructed as simply as possible and be producible as cost-effectively as possible.

DETAILED DESCRIPTION OF THE INVENTION

Figure 1:
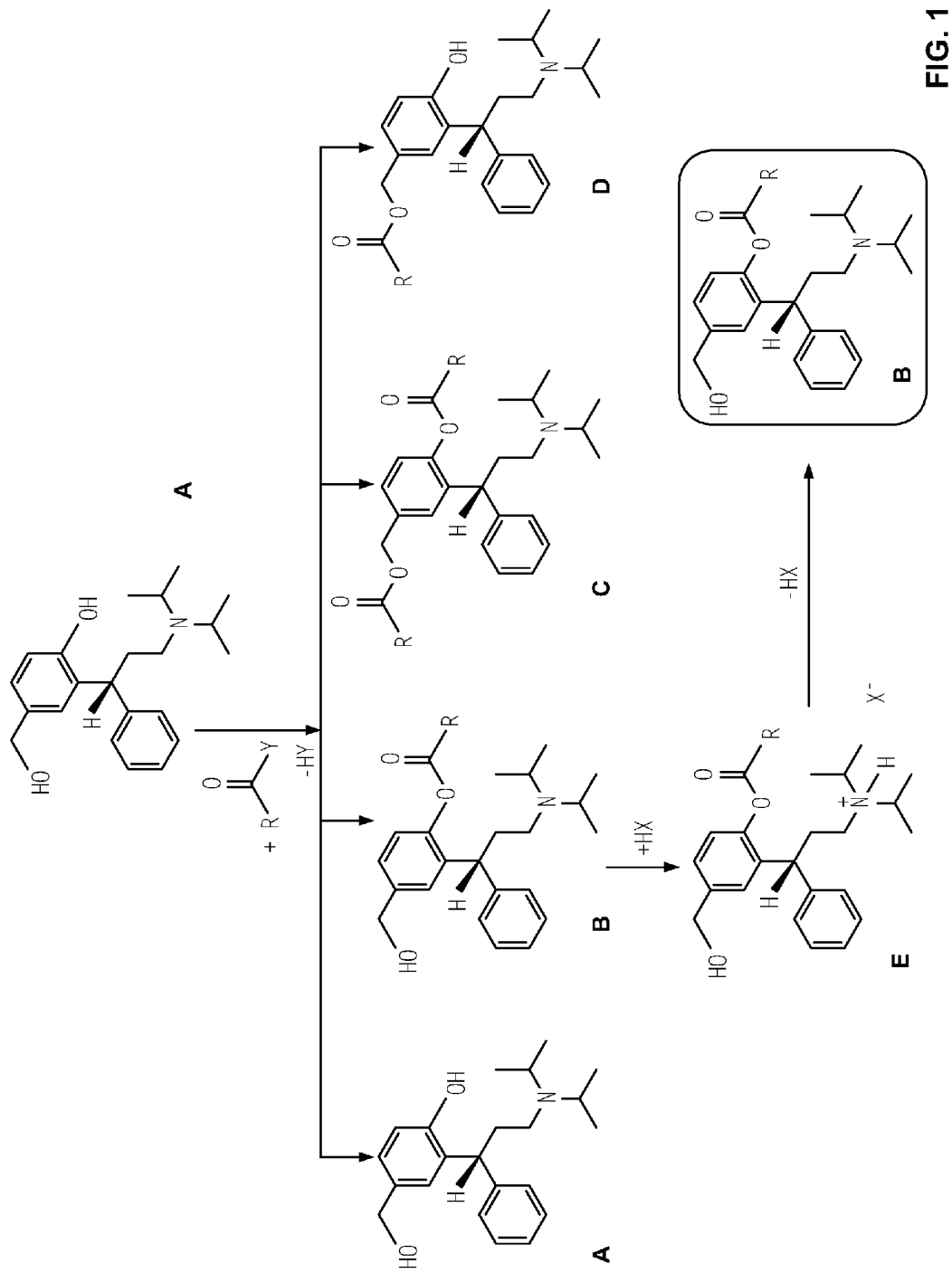
FIG. 1 illustrates a general procedure that can be used for the manufacture of fesoterodine base.

The suitability of a transdermal medicine for the controlled administration of active ingredients, preferably for several days, is now being influenced by a number of parameters and requirements, for example,
The type of transdermal preparation (ointment, gel, patch, spray).
Control of the release of the active ingredient (passive diffusion, iontophoresis, ultrasound, electroporation)
Concentration of the active ingredient, loading and saturation of the form of application,
The cutaneous permeability for the active ingredient under occlusive conditions, for example, following application of a patch,
The type of retarding principle that is being used to ensure a continual steady-state flux over one or several days,
The manufacturing procedure of the form of administration,
the required daily dose of the active ingredient,
The use of the active ingredient in optimum form (base, salt, state of aggregation, optical configuration).

A medicine for controlled transdermal delivery is consequently a highly complex system, in which a multitude of factors often have an unforeseeable influence on the properties of the formulation of the active ingredient and the penetration of the skin.

So despite many years of efforts by the pharmaceutical industry, there are still no forms of transdermal administration of an active muscarinic ingredient, such as Oxybutynin or Tolterodin, for example, obtainable on the market today.

Also, the transdermal delivery of the Tolterodin primary metabolites 2-[3-(1,1-diisopropylamino)-1-phenylpropyl]-4-(hydroxy methyl)phenol is still not yet clinically possible due to its very low rate of penetration through the human skin (see Table 1).

There is a suggestion implicated in WO 99/58478 that in principle 3,3-diphenylpropylamine-monoesters can permeate the skin if a solution of a substance is subjected to a test in compliance with Thiemessen (Acta Pharm Technol 34, 1999, 99). However, WO 99/58478 does not contain any teaching on how a device for the transdermal administration has to be arranged in order to achieve a most constant transdermal flux of the 3,3-diphenylpropylamine monoester active ingredient on patients over a longer period of time.

Moreover, due to low flux rates these transdermal forms of drugs, which were manufactured using the known high purity salts from 3,3-diphenylpropylamine monoesters from WO 01/35957 are proving themselves in costly series of measurements to be therapeutically unsuitable (Table 1).

It was a surprise now to discover, however, that a compound of the general Formula I

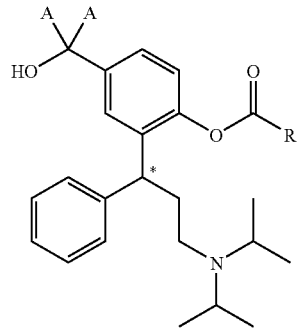

Formula I in which A means hydrogen or deuterium, R stands for a group $C_{1-6}$-alkyl, $C_{3-6}$-cycloalkyl or phenyl which may each be substituted with fluorine, chlorine, bromine, iodine, hydroxyl, oxo or deuterium and where the C-atom marked with a star "*" is present in the (R)-configuration,
can be transported at a steady flux rate through the human skin during a timeframe of at least 24 hours in an amount of 0.5-20 mg sufficient for therapeutic treatment of the overactive bladder, if the combination of the general Formula I is introduced into a transdermal device in a sufficient quantity as a free base in a polymer layer, preferably a self-adhesive polymer layer (adhesive matrix).

Using such a simply constructed, flat shaped device with a surface of a maximum around 50 $cm^2$ it is surprisingly possible, to make the clinically relevant dosing spectrum of the combinations of the general Formula I transdermally available.

One object of the invention is therefore a device for the transdermal delivery of a compound of the Formula I

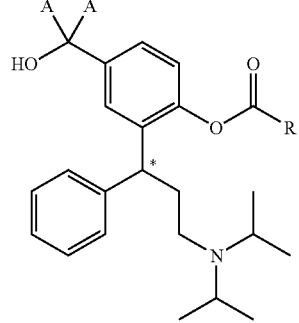

Formula I in which A means hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" is present in the (R)-configuration, characterized by the fact that the combination of the general Formula I is present in a polymer layer, preferably in a self-adhesive polymer layer (adhesive matrix), dissolved or dispersed and is released through the human skin in a flux rate of 0.5-20 mg per day.

More advantageously the active ingredient is introduced into the polymer layer, for example, to the adhesive matrix in the form of the free base.

In the sense of the invention it is understood by the expression "free base" that less than 20 percent by weight, preferably less than 10%, 5% or 3%, especially preferred less than 1% of the compound of the general Formula I is present in the salt form.

If the high purity salts from 3,3-diphenylpropylamine derivates known from WO 01/35957, for example, the fumarate salt from fesoterodine, are introduced into the polymer layer, this does only lead to flux rates not sufficient for transdermal treatment. Even the addition of loaded molecules such as silicates or chitosan, for example, or of skin penetration amplifiers like oleic acid or polyglycol monolaurate to the matrices containing the active ingredient salt does not lead to satisfactory flux rates (Table 1).

Generally speaking, even an in-situ release of the base from the corresponding salt through the addition of calcium silicate during production of the adhesive matrix, as described in WO 94/07486, would not lead to the flux rates through the human skin desired (Table 1). The in-situ conversion to the free base is generally not absolute so that too high a proportion of the active ingredient in its protonated form is present in the matrix.

The compound of the general Formula I should therefore be added to the polymer matrix mass, preferably already in the form of the free base at the time of the manufacture of the inventive device. In this instance all matrices tested led to therapeutically relevant flux rates (Table 1)

The salt portion of the general Formula I should therefore preferably be as low as possible. Typically the part of the compound of the general Formula I, which is introduced into the polymer matrix in salt form, should total less than 20 percent by weight, preferably less than 10%, 5% or 3% and especially preferably less than 1% of the total weight of the active ingredient used.

In compliance with the invention the compounds of the general Formula I are present to over 90%, preferably to over 95%, especially preferably to over 99% as optically, high purity enantiomers in the conformational structure (R). This means that less than 10%, preferably less than 3%, especially preferably less than 1% of the compounds are present in the conformational structure (S).

In an advantageous form of execution of the invention the polymer matrix has a weight of 30-300 $g/m^3$, contains 50-95% by weight of a polymer, preferably a self-adhesive polymer (contact adhesive) and 5-40% by weight of a compound of the general Formula I (each time based on the total weight of the polymer matrix).

In an especially preferred form of execution of the invention the device is characterized in that it
(a) exhibits a base of a maximum 50 $cm^2$,
(b) incorporates a self-adhesive polymer layer, which
   (b1) exhibits a weight of 30-300 $g/m^2$,
   (b2) contains 50-95% by weight of a contact adhesive,
   (b3) contains a compound of the general Formula I in a concentration of 5-40 percent by weight based on the total weight of the polymer layer and especially preferred,
(c) the said compound of the general Formula I delivers at least 4 $\mu g/cm^2$/hour with a steady-state flux rate through the human skin over a time period of at least 24 hours.

In a further preferred form of execution of the invention the medicine contains a compound of the general Formula I where R is selected out of the $C_1$-$C_6$-alkyl group, in particular methyl, ethyl, 1-propyl, isopropyl (i-Pr), 1-butyl, 2-butyl, tertiary-butyl, iso-butyl, pentyl and hexyl.

TABLE 1

| Lot-No | Contact adhesive | Procedure | Loading of the active ingredient (Percent by weight fesoterodine) | Matrix weight ($g/m^2$) | Flux $\mu g/cm^2$/Day (in steady state; after 24 hours) Mouse Skin | Human skin |
|---|---|---|---|---|---|---|
| 20111080[1] | Acrylate | Solvent | 15 | 100 | 705 | n.d. |
| 20302060[1] | Acrylate | Solvent | 15 | 87 | n.d. | 332.64 |
| 20111085[1] | EVA | Hotmelt | 15 | 84 | 510 | 323.7 |
| 20111086[1] | Silicone | Hotmelt | 15 | 63 | 495 | n.d. |
| 20302062[1] | Silicone | Hotmelt | 15 | 100 | n.d. | 544.89 |
| 20111087[1] | SxS | Hotmelt | 15 | 89 | 460 | 383.8 |
| 20302063[1] | Silicone + PVAc[6] | Hotmelt | 15 | 83 | n.d. | 501.09 |
| 20002031[2] | Acrylate | Solvent | 15 Fumarate | 105 | 27 | n.d. |
| 20104035[2,3] | Acrylate/OL | Solvent | 15 Fumarate | 110 | 84 | n.d. |
| 20106061[4] | Silicone | Solvent | 15 Fumarate | 60 | n.d. | 24.2 |
| 20106043[5] | Silicone | Hotmelt | 15 DiOH[5] | 101 | n.d. | 2.3 | n.d. = not determined;
[1] = fesoterodine was added to the matrix as the free base;
[2] = Comparison example manufactured through the use of fesoterodine-fumarate salt;
[3] = Comparison example manufactured through the use of fesoterodine-fumarate salt with oleic acid as the permeation enhancer;
[4] = Comparison example manufactured through the in-situ release of the base from the fumarate salt into the adhesive matrix;
[5] = Comparison example manufactured through the use of the dihydroxy metabolites (2-[3-(1,1-diisopropylamino)-1-phenylpropyl]-4-(hydroxymethyl)phenol) from fesoterodine;
[6] PVAc = Poly Vinyl Acetate.

In a notably preferred form of execution of the invention the medicine for transdermal delivery contains (R)-2-[3-(1,1-diisopropylamino)-1-phenylpropyl]-4-(hydroxymethyl) phenyl isobutyrate (fesoterodine) in its polymer matrix as the active ingredient.

In compliance with the invention the expression "$C_{1-6}$-alkyl" denotes a straight chain or a branched chain hydrocarbon group with 1-6 C-atoms.

The expression "$C_{3-10}$-cycloalkyl" is understood to mean a cyclical hydrocarbon group with 3-10 hydrocarbon atoms.

In this patent application copolymers are also subsumed under the expression "polymer".

In this invention a layer, stratum or paste that contains one or several polymers is comprehended under the expression "polymer matrix". If the polymer matrix is self-adhesive it is also identified as an "adhesive matrix".

In this patent application the expression "total weight of the polymer mix" is understood to mean the weight of the polymer matrix including the active ingredient introduced into it and possible auxiliary agents.

In the case of the inventive device it involves a customary, flat shaped transdermal device/form of medicine of the matrix type, meaning the active ingredient is present either embedded in a polymer layer or polymer paste (dissolved or dispersed).

Preferably the device contains a monolithic adhesive matrix into which the active ingredient is embedded.

Figure 4:
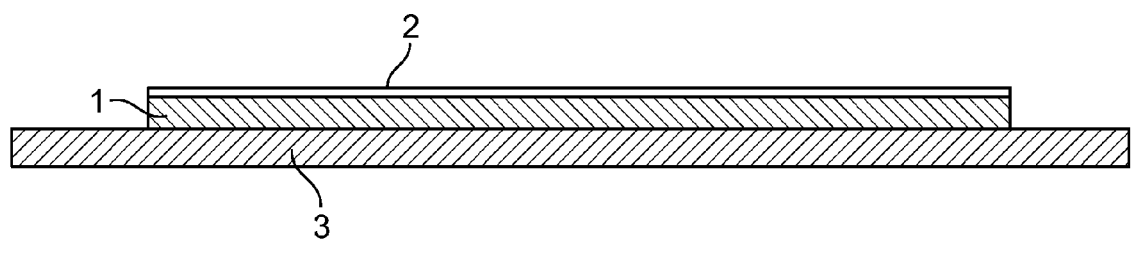
FIG. 4 illustrates the typical structure of a monolithic TTS.

An example for a typical structure of a monolithic transdermal device is reproduced in FIG. 4. The device described there consists of the adhesive matrix, which contains the active ingredient (1), a backing which is inert and impermeable for the ingredients of the adhesive matrix, wherein said backing after the administration of the patch onto the skin of the patient finds itself on the site of the patch which is remote from the skin (2) as well as a layer for protection of the adhesive matrix in storage, detachable immediately before use (3).

In compliance with the invention the surface of the transdermal device totals a maximum of 50 cm², preferably a maximum of 40 cm². Especially preferred patch sizes lie between 5 and 35 cm², notably especially preferred between 10 and 30 cm².

The polymer matrix, for example, the adhesive matrix, containing the contact adhesive and the active ingredient, typically has a thickness of 30-300 μm, preferably of 40-200 μm and an average weight of 30-300 g/m², preferably from 40-200 g/m².

The active ingredient in compliance with the invention is present in the polymer matrix, preferably in the adhesive matrix in a concentration of 5-40 percent by weight, preferably 7-30 percent by weight and especially preferably 8-20 percent by weight based on the total weight of the adhesive matrix when the device/the medicine, for example, is intended for a 2-3 day application. If a medicine is to be manufactured for a 7-day administration of a compound of the general Formula I then active ingredient concentrations above 15 percent by weight, preferably 20-40 percent by weight are used.

The active ingredient load of the polymer layer, for example, the adhesive matrix may therefore lie between 0.15 and 12 mg/cm². The preferred loading strengths are loads between 0.25 and 7.5 mg/cm², especially preferred between 0.32 and 4 mg/cm². The loading is preferably down to a minimum of 2 mg/cm² in the case of devices for 7-day applications.

In one form of execution of the invention the free base of the general Formula I is present in a concentration that in the process leads to the over-saturation of the respective polymer matrix with the active ingredient. This may lead to the formation of the so-called micro reservoirs, which are present in the matrix in the shape of drops, in particular in a hydrophobic matrix, for example, of the silicone type.

In this situation it is preferred that the micro reservoirs containing the active ingredient exhibit the most uniform, average size distribution possible of a maximum of 50% of the layer thickness of the matrix. This is able to be ensured through an intensive homogenization of the matrix so that especially preferably an average drop in size of up to 30 μm results.

In a different form of execution of the invention the active ingredient is present in a concentration in which it is completely dissolved in the matrix, for example, in an acrylate matrix.

In principle, the free bases of the general Formula I used for the manufacture of the devices in compliance with the invention are able to be acquired as published in WO 99/58478. For this purpose (R)-2-(3-diisopropylamino-1-phenylpropyl)-4-hydroxymethylphenol is converted under alkaline conditions with a suitable acid chloride, for example, isobutyric acid chloride.

However, this reaction only leads to approximately 90%, up to a maximum of approximately 94%, of the desired main product (B). The product consistently contains 6-10% impurities of the starting substance (A) as well as undesired reaction products in the form of the corresponding di-ester (C) or through the formation of the monoester (D) of the 4-hydroxy group (see FIG. 1) as well as by polymerization.

However, as a general rule a purity of above 97 percent by weight is preferred for pharmaceutical preparations.

It was found that a free base of the general Formula I could be yielded in a purity of consistently above 97 percent by weight, preferably above 98 percent by weight, especially preferably above 98.5 percent by weight and notably especially preferably above 99 percent by weight normally with a high yield above 90 mol % if the free base is manufactured by releasing it with an appropriate reagency from a high purity, crystalline salt.

In this application the expression "high purity" is understood to mean a degree of purity of at least 97 percent by weight, preferably above 98 percent by weight, especially preferably above 98.5 percent by weight and notably especially preferably above 99 percent by weight. In the course of this the degree of purity is determined as described in the techniques section.

The high purity bases of the general Formula I in compliance with the invention can be manufactured by releasing them from the high purity, crystalline salts of the general Formula II:

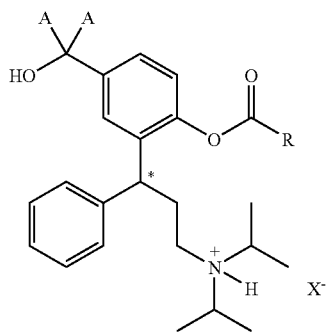

Formula II where A and R have the significance given above, X⁻ is the acid residue of a physiologically compatible acid and where the C-atom marked with "*" (a star) can be present in the (R)-configuration, in the (S)-configuration or as a mixture thereof.

In the course of this the anion of the subsequently named acids comes into consideration as an acid residue X⁻: hydrochloric acid, hydrobromic acid, phosphoric acid, sulfuric acid, nitric acid, acetic acid, propionic acid, palmitic acid, stearic acid, maleic acid, fumaric acid, oxalic acid, succinic acid, DL-malic acid, L-(−)-malic acid, D-(+)-malic acid, DL-tartaric acid, L-(+)-tartaric acid, D-(−)-tartaric acid, citric acid, L-aspartic acid, L-(+)-ascorbic acid, D-(+)-glucuronic acid, 2-oxopropionic acid (pyruvic acid), furane-2-carboxylic acid (pyromucic acid), benzoic acid, 4-hydroxybenzoic acid, salicylic acid, vanillic acid, 4-hydroxycinnamic acid, gallic acid, hippuric acid N-benzoyl-glycin), aceturic acid (N-acetyl glycine), phloretin acid (3-(4-Hydroxyphenyl)-propionic acid), phthalic acid, methane-sulphonic acid or orotic acid, where the acid anions hydrogen fumarate and hydrochloride are especially preferred.

The corresponding high purity bases are released from this high purity compound of the general Formula II through the addition of the appropriate reagents.

The release reagents are, for example; alkaline compounds from the group of
hydroxides, carbonates and alkaline-, alkaline earth- or ammonium hydrogen carbonates
amines, polyamines and alkaline polyamino acids, that may also be present both in a solution and fixed onto carriers,
alkaline ionic exchangers,
where weak alkaline compounds with a $PK_B$ of 8-11 are preferred.

An alkaline-, earth alkaline or ammonium hydrogen carbonate [sic] is especially preferred as the "releasing reagent", where sodium hydrogen carbonate is notably especially preferred.

In a preferred manufacturing process the salt of the Formula II is first absorbed in water and laced with a base releasing agent, for example, a hydrogen carbonate. This is then extracted by shaking using an appropriate solvent, and the organic phase evaporated to a low small bulk until the high purity base of the Formula I remains behind as a viscous oil. Such a process is shown in more detail in Example Execution C.

Solvents that are suitable for such a process are in particular dichloromethane, tertiary-butyl-methyl ether, diethyl ether, ethylmethylketone as well as toluene, where dichloromethane is preferred.

In an alternative manufacturing process the high purity salt of the Formula II is absorbed in an appropriate solvent and then conducted over a carrier, which contains ionic exchangers, for example. The eluate then contains the high purity base of the general Formula I.

(R)-2-[3-(1,1-diisopropylamino)-1-phenylpropyl]-4-(hydroxymethyl)phenyl isobutyrate hydrogen fumarate is especially preferred for use as the initial compound of the Formula II for the production of the high purity free base of (R)-2-[3-(1,1-diisopropylamino)-1-phenylpropyl]-4-(hydroxymethyl)phenyl isobutyrate.

The production of the high purity salts of the Formula II is known from WO 01/35957. For this purpose a solution of 2-[3-(1,1-diisopropylamino)-1-phenylpropyl]-4-(hydroxymethyl)phenol is converted in a base solution with an acid chloride, for example, isobutyric acid chloride. The resulting base with a low purity content is then laced with an acid, for example, fumaric acid, while being heated. The resulting salt of the general Formula II can then be crystallized out into appropriate solvents. The crystals are then dissolved again and re-crystallized. This process can be repeated if necessary until a compound of the Formula II is obtained with the desired degree of purity. The high purity base of the Formula I is released from these salts as described above.

| Process Step [a] | Purity B or E (%) |
|---|---|
| 1. Chemical synthesis of B from A | 94.37 |
| 2. Production of the salt E from B (1) | 92.58 |
| 3. Re-crystallization of the salt E from (2.) | 99.32 |
| 4. Released high purity base B from E (3.) | 99.14 |

[a] A, B, C, E: R = i-Pr, see FIG. 1

The process described allows for the first time the efficient production of the free base of the general Formula I in high purity form and with it also for the first time the application of the high purity bases of the general Formula I for the production of the inventive devices for controlled transdermal delivery.

One preferred object of the invention is therefore a device for the transdermal delivery of a compound of the Formula I

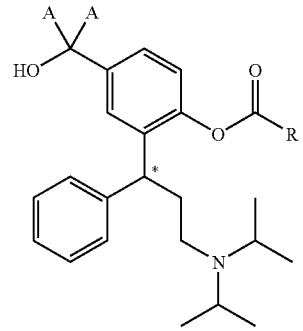

Formula I in which A means hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" is present in the (R)-configuration, characterized by the fact the fact that the device is manufactured by a compound of the general Formula I being introduced into a polymer layer, preferably into a self-adhesive polymer matrix (adhesive matrix) as a free base with a degree of purity of 97 percent by weight, preferably above 98 percent by weight, especially preferably above 98.5 percent by weight and notably especially preferably above 99 percent by weight.

One especially preferred object of the invention is a flat-shaped device for the transdermal delivery of a compound of the Formula I

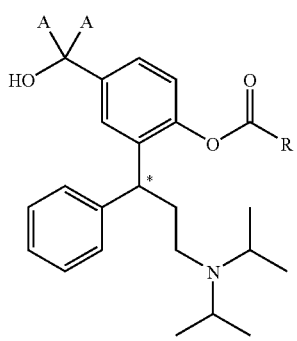

Formula I in which A means hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" is present in the (R)-configuration, characterized by the fact the fact that the device incorporates
(a) an area of a maximum of 50 cm'
(b) a self-adhesive polymer matrix, which
  (b1) exhibits a weight of 30-300 $g/m^2$,
  (b2) contains 50-95% by weight of a contact adhesive,
(c) a compound of the general Formula I dissolved or dispersed in the self-adhesive polymer matrix (b), which
  (c1) is present in a concentration of 5-40% based on the total weight of the polymer matrix,
    and is introduced to said polymer layer
  (c2) preferably in the form of the free base with a salt content of less than 10 percent by weight as well as
  (c3) preferably in a degree of purity of above 97 percent by weight, preferably above 98 percent by weight especially preferably above 98.5 percent by weight and notably especially preferably above 99 percent by weight.

In an especially preferred form of execution the compound introduced into the polymer layer is the high purity free base from (R)-2-[3-(1,1-diisopropylamino)-1-phenylpropyl]-4-(hydroxymethyl)phenyl isobutyrate (fesoterodine).

Various polymers known in patch technology are qualified for production of the polymer layer, where the use of contact adhesive polymers is preferred, as outlined below and in more detail.

Figure 3:
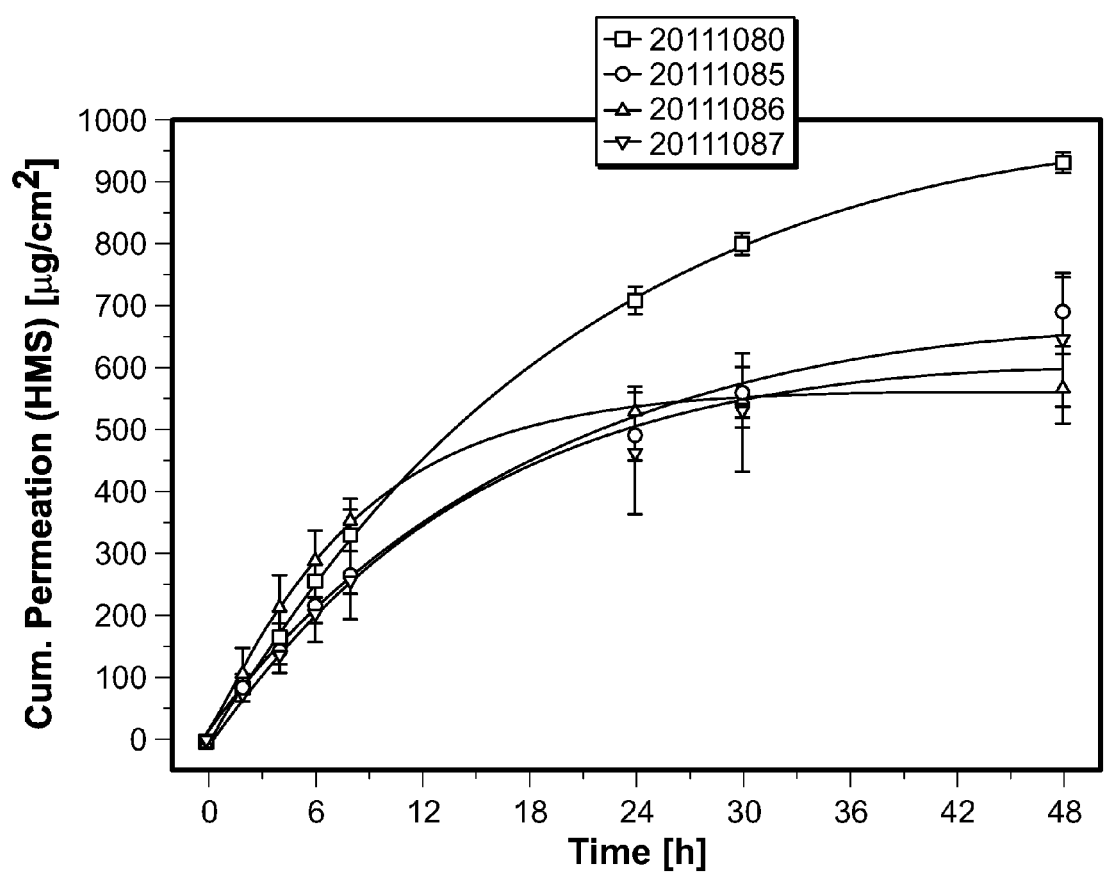
FIG. 3 illustrates the in-vitro flux rate through mouse skin for the high purity free base of fesoterodine.

Generally speaking, the flux of a particular active ingredient through the human skin is essentially determined through the matrix used in which the active ingredient is embedded. Contrary to expectations in this case all of the self-adhesive matrices used in-vitro led to high flux rates through mammalian skin (FIG. 3, Table 1). The reasons for this are the extraordinarily good skin penetrating properties of the free bases of the general Formula I in general and of the fesoterodine in particular.

It is assumed that on average an effective daily dose of 0.5-20 mg, normally of at least 3 mg/day, for example, 3-20 mg/day, preferably 3-15 mg/day and especially preferably 4-12 mg/day of the active ingredient or of the active metabolites (R-2-[3-(1,1-diisopropylamino)-1-phenylpropyl]-4-(hydroxymethyl)-phenol has to be transported through the skin of a patient. In exceptional cases a lower daily dose of 0.5-3 mg/day or a higher dose of above 20 mg/day may be adequate or required respectively.

Table 3 shows that TTS in those cases in which the high purity base of (R)-fesoterodine in an amount of 15 percent by weight was introduced into appropriate adhesive matrices of the SXS or EVA type lead to flux rates that make therapeutically desired daily doses with the corresponding application surface of 5-50 $cm^2$ possible in the case of the trials using in-vitro human skin:

| Flux rate fesoterodine through human skin (mg/day) based on the TTS size | | | | | | |
|---|---|---|---|---|---|---|
| | TTS size | | | | | |
| Contact adhesive | 5 $cm^2$ | 10 $cm^2$ | 20 $cm^2$ | 30 $cm^2$ | 40 $cm^2$ | 50 $cm^2$ |
| EVA | 1.6 | 3.2 | 6.5 | 9.7 | 13 | 16 |
| SXS | 1.9 | 3.8 | 7.6 | 11.4 | 15.2 | 19 |
| Silicone/Cer + PVAc | 2.5 | 5 | 10 | 15 | 20 | 25 |
| Acrylate (Durotak 87-4287) | 1.7 | 3.3 | 6.6 | 10 | 13.3 | 16.7 |

Figure 2:
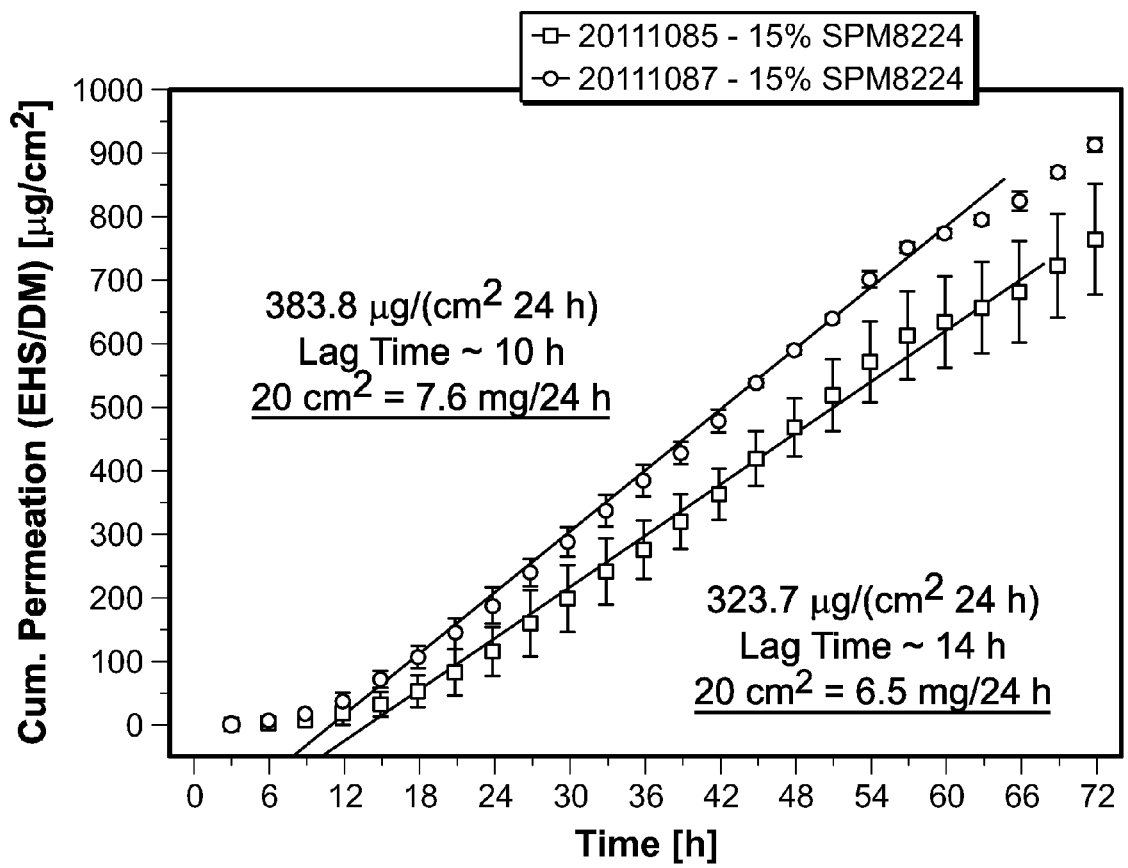
FIG. 2 illustrates the in-vitro flux rate through human skin for the high purity free base of fesoterodine.

Surprisingly, in compliance with the invention, the medicine containing fesoterodine as a free base delivered transdermal, steady-state flux rates through the human skin of above 300 $\mu m/cm^2/day$ in the matrices tested meaning that above 13 $\mu m/cm^2/hour$ over a time period of at least 48 hours (FIG. 2).

The in-vitro flux rates through human skin from the polymer matrices in compliance with the invention exceed those from the free solution, which were given in WO 00/58478, surprisingly clearly.

Through the constant high flux rates the matrices in compliance with the invention facilitate, surprisingly though, the production of devices for the controlled transdermal delivery of the compounds of the general Formula I, in particular (R)-2-[3-(1,1-diisopropylamino)-1-phenylpropyl]-4-(hydroxymethyl)phenyl isobutyrate (fesoterodine free base) across the entire therapeutically relevant range of doses from 0.5-20 mg/day and at steady flux rates over a minimum of 24 hours, without significantly transgressing above a total surface of 50 $cm^2$.

One aspect of this invention is thus a medicine for the transdermal delivery of a compound of the general Formula I in the form of the free base, in particular (R)-2-[3-(1,1-diisopropylamino)-1-phenylpropyl]-4-(hydroxymethyl)phenyl isobutyrate (fesoterodine free base) over a time period of at least 24 hours, preferably at least 48 hours, at a steady flux rate of more than 125 µg/hour, preferably 125-850 µg/hour, especially preferably 125-650 µg/hour and notably especially preferably 150-500 µg/hour.

Another aspect of the invention is a medicine for the steady transdermal delivery of a compound of the general Formula I in the form of the free base, in particular (R)-2-[3-(1,1-diisopropylamino)-1-phenylpropyl]-4-(hydroxymethyl)phenyl isobutyrate (fesoterodine free base) over a time period of at least 24 hours, preferably at least 48 hours, in a steady flux rate of more than 4 $\mu g/cm^2/hour$, preferably 6 $g/cm^2/hour$, especially preferably of more than 8 $\mu g/cm^2/hour$, 10 $\mu g/cm^2/hour$ or more than 12 $\mu g/cm^2/hour$ where the flux rates are determined according to Tanojo in a model of human skin in-vitro as specified in Example Execution 3.2.

The human skin in-vitro model used in this invention according to Tanojo has proven itself to be an excellent model in which the in-vitro flux rates measured correlate with the in-vivo flux rates and plasma levels, which were measured in several clinical studies with various active ingredients containing aminos.

The daily flux rates measured using the inventive devices correspond with the amount proved in clinical studies in most of the patients to be the optimum effective dose of (R)-2-[3-(1,1-diisopropylamino)-1-phenylpropyl]-4-(hydroxymethyl)phenyl isobutyrate (fesoterodine) in the case of oral administration (approximately 4-12 mg per day) and leads to therapeutic plasma levels of 1-15 ng/ml, preferably of 2-12 ng/ml, especially preferably of 3-10 ng/ml of the metabolites (R)-2-[3-(1,1-diisopropylamino)-1-phenylpropyl]-4-(hydroxymethyl)phenol.

Another aspect of the invention is therefore a medicine for the transdermal delivery of a compound of the general Formula I, in particular (R)-2-[3-(1,1-diisopropylamino)-1-phenylpropyl]-4-(hydroxymethyl)phenyl isobutyrate (fesoterodine free base) at a flux rate that leads to the production of a steady plasma level of 1-15 ng/ml, preferably of 2-12 ng/ml, especially preferably 3-10 ng/ml of the metabolites (R)-2-[3-(1,1-diisopropylamino)-1-phenylpropyl]-4-(hydroxymethyl)phenol over a time period of at least 24 hours, preferably at least 36 hours.

In this patent application the expression "steady-state" is understood to mean a dynamic equilibrium which adjusts itself after an initial lag phase following application for the first time of the inventive device.

A "steady state flux rate" is understood to mean a flux rate that adjusts after the initial lag phase.

In this patent application the expression "constant flux" rate is understood to mean a steady-state flux rate in the case of which a compound of the general Formula I is transported at an average flux rate through human skin, which exhibits an intra-individual variability CV over the time of a maximum of 30%, preferably a maximum of 20% or even a maximum of 10%, where CV is determined according to the equation CV (sd:x)×100% (see the Cawello (ED) calculation in "Parameters for Compartment-free Pharmacokinetics", Shaker Verlag, Aachen, 1999, Page 112). In the course of this a daily dose is administered at an average flux rate of daily dose: 24 (mg/hour) with a CV of 30%. To the skilled person it is clear that a steady flux rate is only adjusted following an initial burst effect phase ("lag phase") after application for the first time of the device. The lag phase is therefore not taken into consideration in the calculation of the steady flux rate.

In this patent application, unless expressly stated otherwise, the expression "flux rate through human skin" is understood to mean a flux rate that was measured according to Tanojo in an in-vitro human skin model as described in Example Execution 3.2.

In this patent application the expression "constant plasma level" is understood to mean that the patient exhibits a defined plasma level of the active metabolites following an initial burst effect phase after the first time application of the inventive medicine above a minimum of 80%, preferably at least 85% and especially preferably at least 90% of the time of the administration of the inventive medicine.

The devices in compliance with the invention generally contain 50-95 percent by weight, preferably 70-90 percent by weight of a polymer in the polymer layer, preferably of a pressure sensitive polymer ("contact adhesive").

In the course of this the contact adhesives known in patch technology are qualified in principle as a base for a self-adhesive polymer layer, such as for example, silicone adhesive, ethyl vinyl acetate (EVA-) adhesive, styrene-block-copolymer (SXS) adhesive, acrylate adhesive, polyurethane adhesive, vinyl acetate adhesive as well as adhesive gums, for example, polyisobutylene, polybutadiene, neoprene or polyisoprene as well as appropriate mixtures of these adhesive substances.

One object of the invention is therefore a device for the transdermal delivery of a compound of the Formula I

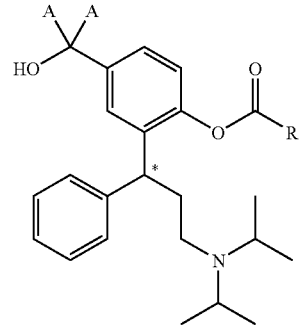

Formula I in which A means hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chorine, bromine, iodine, nitro, amino, hydroxyl, oxo, mercapto or deuterium and where the C-atom marked with a star "*" is present in the (R)-configuration, which is characterized by the fact that a compound of the general Formula I preferably in the form of the free base is introduced into a self adhesive polymer layer, where the self-adhesive polymer layer incorporates at least one contact adhesive from the group of silicone adhesive, ethyl vinyl acetate (EVA)-adhesive, styrene block copolymer (SXS)-adhesive, acrylate adhesive, polyurethane adhesive, vinyl acetate adhesive, of the adhesive gums, for example, polyisobutylene, polybutadiene, neoprene or polyisoprene or suitable mixtures of these adhesive substances.

In principle the manufacture of the polymer layers containing an active ingredient may take place in a solvent procedure or in a hot melt procedure.

In a solvent procedure the active ingredient and the polymer as well as any other auxiliary agents are each dissolved in solvents and then mixed with one another. The mixture is then spread out on foil and the solvent evaporated by gentle heating.

In a hot melt procedure the polymers and any auxiliary agents are thermally melted and mixed without the use of any solvents and the meltings spread out on foil. The active ingredient is normally introduced directly into the liquid melt. Those polymers which are sufficiently liquid at processing temperatures from up to 200° C., meaning that they preferably exhibit a dynamic viscosity of below 100 Pa's, are particularly suitable for the hot melt procedure. The dynamic viscosity may be determined in the process as described in U.S. Pat. No. 5,328,696.

The compounds of the general Formula I, in particular fesoterodine, prove themselves to be surprisingly stable at the processing temperatures up to 200° C. in the hot melt procedure.

The known polymers of the acrylate type, the SxS type, the EVA type as well as the silicone type are particularly suitable as contact adhesives, especially the hot-meltable silicone softener mixes. These adhesives exhibit a satisfactory adhesion on human skin and provide excellent flux rates regarding the high purity bases of the general Formula I, especially with regard to fesoterodine. These adhesives are very compatible with the skin and suitable for pharmaceutical purposes. The properties and the manufacture of these preferred contact adhesives will be explained more closely in the following as examples:

Silicone Adhesives:

The preferred silicone adhesives are amine resistant, pressure sensitive, polymeric organosiloxane adhesives.

In most cases silicone contact adhesives represent polymeric dimethyl siloxanes, however in principle other organic residues, such as ethyl or phenyl groups for example, may also be available instead of the methyl groups. Amine resistant silicone contact adhesives are generally distinguishable in that they contain no or only contain a few free silanol functions because the Si—OH-groups were alkylated. Such adhesives are described in EP 180 377. Condensates or mixtures of silicone resins and polymeric organosiloxane adhesives such as described in U.S. RE 35,474 are especially preferred adhesives.

Suitable adhesive substances are sold, for example, by Dow Corning as the so-called Bio-PSA adhesive substances. In the process mixtures of the contact adhesive Bio PSA Q7-4301 and Q7-4201 are particularly suitable, especially in a 40:60 to 60:40 ratio.

Patch matrices based on silicone adhesives are processed predominantly in solvent based procedures. For this purpose a solution of contact adhesives and active ingredient are manufactured in a first step in an organic solvent or a mixture of solvents. In a second step the solution is spread out and laminated and the solvent is then removed. Such a procedure is described as an example in WO 99/49852.

An alternative procedure that dispenses with the use of organic solvents is the hot melt procedure. In this procedure the polymer or the contact adhesive are melted at temperatures between 70 and 200° C., preferably between 90 and 160° C. and especially preferably between 100 and 150° C. and the active ingredient introduced into the homogenized matrix melt. After a brief homogenization the adhesive matrix that contains the active ingredient is cooled again so that the active ingredient is exposed to a thermal load in general for less than 5 minutes, if desired even for 4, 3, 2 or even for less than 1 minute. Following this the active ingredient is present in the solidified polymer melt. During the process the active ingredient is broadly shielded from critical environmental influences (light, oxygen).

This procedure has the advantage over the solvent based procedure that the high purity bases of the general Formula I are not exposed to any solvent influences but instead are able to be added immediately into the hot melt where after a short homogenization they are stabilized in the cooling polymer matrix. The hot melt procedure is preferably carried out in an extruder, for example in a twin screw extruder, as described in WO 99/48493.

At the above mentioned processing temperatures the silicone adhesives are too viscous, meaning they have a dynamic viscosity of above 150 Pa's. Various procedures were described in the patent literature to make the viscosity of the silicone adhesives hot-meltable through the admixing of suitable additives (softeners). Examples of those softeners for silicone are glycerol monolaurate or lauryl acetate as described in EP 835 136, waxes of the formula R—C(O)—OR' as described in EP 360 467, alkylmethyl siloxane waxes as described in EP 524 775, siloxanated polyether waxes as described in EP 663 431 or organic waxes as described in U.S. RE 36,754.

Generally speaking, the softeners are added to the silicone adhesive in a quantity of 1-30 percent by weight based on the total mixture of the hot-meltable adhesive mixture. The preferred softeners are organic waxes as described in U.S. RE 36,754, for example, ozokerite wax, ceresine wax, paraffin wax, candelilla wax, carnauba wax, beeswax or mixtures of these waxes, where ozokerite and ceresine are notably, especially preferred.

Ready-made hot-meltable silicone contact adhesives, in particular mixtures of silicone contact adhesives with ceresine or ozokerite may be obtained from Dow Corning, Michigan. For example, through the addition of 10 percent by weight ceresine wax to a silicone contact adhesive of type Q7-4301, it is possible to lower the dynamic viscosity of the resulting contact adhesive mixture from above 200 Pa's to below 50 Pa's at a processing temperature of 150° C. Such a silicone based contact adhesive mixture can be processed very well in a temperature range of from 70° C. to 200° C. and in particular in the range between 100° C. and 150° C. in a hot melt procedure.

Surprisingly it was determined that hot-meltable silicone contact adhesives are excellently suited for the transdermal delivery of the compounds of the general Formula I.

One object of the invention is therefore a device for the transdermal delivery of a compound of the Formula I

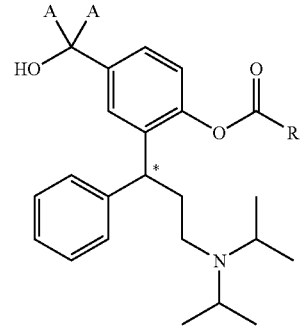

Formula I in which A means hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "1" is present in the (R)-configuration, characterized by the fact that the combination of the general Formula I is present in a self adhesive polymer layer (adhesive matrix), where the adhesive matrix incorporates an amino resistant silicone.

The compound of the Formula I is preferably introduced into the silicone matrix in the form of the free base, especially preferably in the form of the high purity free base.

The silicone based matrix in compliance with the invention contains fesoterodine as the active ingredient.

In an especially preferred form of execution of the invention the adhesive matrix is based on a hot-meltable mixture of a silicone based contact adhesive and at least one softener, in particular an organic wax, for example, ozokerite.

A further aspect of the invention is a medicine for the transdermal delivery of a compound of the general Formula I comprising an adhesive matrix that comprises:
(a) 50-99 percent by weight of a contact adhesive mixture consisting of
  (i) 70-99 percent by weight of an amino resistant silicone adhesive,
  (ii) 1-30 percent by weight, preferably 3-15 percent by weight of an appropriate softener, preferably an organic wax, which especially preferably is selected from the group ozokerite wax, ceresine wax, paraffin wax, candelilla wax, carnauba wax, beeswax or mixtures of these waxes where ozokerite and ceresine are especially preferred, (b) 1-40 percent by weight of a compound of the general Formula I is introduced into the silicone matrix especially preferably in the form of the free base and notably, especially preferred in the form of the high purity free base.

One form of execution of the invention concerns a device for the transdermal delivery of a compound of the Formula I where the compound of the Formula I is dissolved or dispersed in a self-adhesive polymer layer, with the proviso that in cases where the self-adhesive polymer layer consists of silicones in which the free base fesoterodine is dispersed in the form of micro reservoirs that these silicones are either (a) present in a mixture with other non-silicone based polymers or (b) present in a mixture with softeners, where the mixture exhibits a dynamic viscosity of below 100 Pa's and preferably of less than 80 Pa's at temperatures of 200° C.

FIG. 3 shows the in-vitro flux through mouse skin which was achieved using a silicone based patch manufactured in a hot melt procedure that contains ozokerite as a softener for the adhesive matrix and that contains the high purity free base of fesoterodine in the adhesive matrix.

EVA-Adhesives

EVA adhesives are hot-meltable contact adhesives, which are based on ethylene vinyl acetate-copolymers ("EVA-contact adhesive"). EVA-adhesives such as these are described in U.S. Pat. No. 4,144,317 for example. EVA-adhesives feature good adhesive properties, simple manufacture and processing as well as good compatibility with skin. EVA-adhesives can be obtained, for example, from Beardow Adams (13/BA).

What was said under silicones essentially applies for the processing of EVA-contact adhesives in a hot melt procedure, where no softeners have to be added to the EVA-contact adhesives.

One object of the invention is therefore a device for the transdermal delivery of a compound of the Formula I

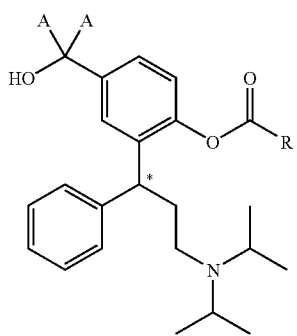

Formula I in which A means hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" is present in the (R)-configuration, characterized by the fact the fact that the combination of the general Formula I is present in a self adhesive polymer layer (adhesive matrix), where the adhesive matrix incorporates a contact adhesive of the EVA-type.

The compound of the Formula I is preferably introduced into the EVA-matrix in the form of the free base, especially preferred in the form of the high purity free base.

It is especially preferable the EVA-matrix contain fesoterodine as the active ingredient.

In an especially preferred form of execution of the invention the EVA-based adhesive matrix is manufactured in a hot melt procedure.

FIGS. 2 and 3 illustrate the in-vitro flux rates through human skin and mouse skin respectively, which were achieved using an EVA-based patch manufactured in a hot melt procedure, in the case of which the high purity base of fesoterodine was introduced into the adhesive matrix.

SxS-Contact Adhesives

SxS contact adhesives may be processed in both solvent based manufacturing procedures and hot melt procedures. In this patent application the term "SxS contact adhesives" is understood to mean styrene block copolymer based adhesives which support non-elastomeric styrene blocks at the ends and elastomeric blocks in the middle. The elastomeric blocks may, for example, consist of polyethylene butylene, polyethylene propylene, polybutadiene, polyisobutylene or polyisopropene.

Suitable SxS adhesives are described in U.S. Pat. No. 5,559,165 or U.S. Pat. No. 5,527,536 for example, and feature good adhesive properties, simple manufacture and processing as well as good compatibility with skin.

SxS contact adhesives may be obtained both commercially (e.g. as Duro Tak 378-3500 at National Starch & Chemical) and manufactured for oneself using hot melt extrusion equipment during the production of patches containing active ingredient.

For instance, for this purpose appropriate amounts (of the following components at a minimum) of a styrene block copolymer (e.g. Shell Kraton GXI 657 or Kraton D-1107CU) are dosed into the extruder with an aliphatic and/or aromatic resin (e.g. Keyser Mackay Regalite R1090 or Regalite R1010 or Regalite R1100) and an oil (e.g. Shell Ondina 933 or Ondina 941) from the individual dosing stations, mixed there and melted. In the last step the active ingredient is dosed into the contact adhesive manufactured in this way in the extruder and the paste laminated on foil sheets. Typical exemplary polymer parts by weight:polymer:resin; oils are e.g. 100:120:20 or 100:200:50. The properties of the SxS contact adhesives can be adapted to the desired properties of the TTS (adhesive strength, minimum cold flow, duration of adherence, releasing profile of the active ingredient) by varying these proportions of the amounts.

One object of the invention is therefore a device for the transdermal delivery of a compound of the Formula I

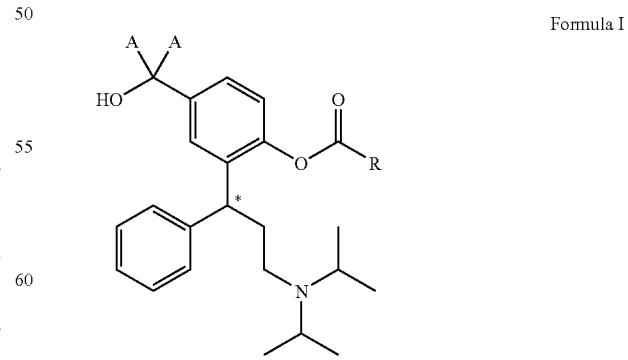

Formula I in which A means hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" is present in the (R)-configuration, characterized by the fact that the combination of the general Formula I is present in a self adhesive polymer layer (adhesive matrix), where the adhesive matrix incorporates a contact adhesive on an SXS base.

The compound of the Formula I is preferably introduced into the SXS matrix in the form of the free base, especially preferred in the form of the high purity free base.

It is especially preferred that the free base of the active ingredient be introduced into the inventive SXS based matrix, notably especially preferred the high purity base of fesoterodine.

In an especially preferred form of execution of the invention the SXS-based adhesive matrix is manufactured in a hot melt procedure.

FIGS. 2 and 3 illustrate the in-vitro flux rates through human skin and mouse skin respectively, which were achieved using an SXS-based patch manufactured in a hot melt procedure, in the case of which the high purity base of fesoterodine was introduced into the adhesive matrix.

Due to the potential oxidative effect of the SXS adhesives, antioxidants are preferably added to SXS-based adhesive matrices. An example for a commercially obtainable, suitable antioxidant is Irganox® (CIBA).

Acrylate Adhesives:

Polyacrylates are produced through the radical polymerization of (meth) acrylic acid derivates, whereby other suitable compounds, such as vinyl acetate, for example, may be used as other monomers. It should be said for clarification that the expression "polyacrylate" used here includes polymers that incorporate units which are based on acrylic acids and/or meth-acrylic acids as well as copolymers and mixtures of them.

As a matter of principle, in the selection of appropriate monomers the resulting contact adhesives can be constituted in such a way that they exhibit specific properties, meaning a favorable solvent capacity for the active ingredient, a desired flexibility of the active ingredient in the matrix as well as a desired transfer-rate through the skin. The transfer rate is significantly limited by the distribution coefficients and the resorption of the active ingredient through the skin.

The pressure sensitive contact adhesive of the polyacrylate type may be a homopolymer and/or copolymer of at least one acrylic acid and/or meth-acrylic acid derivative in the form of a solution in an organic solvent. The polyacrylate type contact adhesive may be cross-linkable or non-cross-linkable. The cross-linking reagent links the polymer chains using reactive groups resulting in an increased cohesion of the contact adhesive.

Preferably the polymer contact adhesive of the polyacrylate type consists of the following monomers at a minimum:

Acrylic acid, acryl amide, hexane-acrylate, 2-ethyl-hexane-acrylate, hydroxy-ethyl-acrylate, octyl-acrylate, butyl-acrylate, ethyl-Acrylate, Glycidyl-acrylate, Methyl-Acrylate, Meth acrylic acid, Methacrylamide, Hexane-Methacrylate, 2-Ethyl-Hexane amide-Acrylate, octyl-Methacrylate, Methyl-Methacrylate, glycidyl-methacrylate, vinyl acetate, vinyl pyrrolidon, allyl-acrylate.

The polymer contact adhesives of the acrylate type, cross-linkable contact adhesives are preferred, which are polymerized from a combination of the following monomers:
2-ethyl-hexyl-acrylate/N-butyl-acrylatelbutyl-acrylate/acrylic acid,
2-ethyl-hexyl-acrylate/N-butyl-acrylate/vinylacetate/acrylic acid,
2-ethyl-hexyl-acrylate/vinylacetate/acrylic acid,
2-ethyl-hexyl-acrylate/vinylacetate/allyl-acrylate,
2-ethyl-hexyl-acrylate/vinylacetate/divinyl-benzol/acrylic acid,
2-ethyl-hexyl-acrylate/vinylacetate/allyl-methacrylate/acrylic acid,
2-ethyl-hexyl-acrylate/vinylacetate/2-hydroxy-ethyl-acrylate,
2-ethyl-hexyl-acrylate/vinylacetate/2-hydroxy-ethyl-methacrylate,
2-ethyl-hexyl-acrylate/fumaric acid-diethyl-ester/acrylic acid,
2-ethyl-hexyl-acrylate/maleic acid-diethyl-ester/2-hydroxy-ethyl-acrylate.

The following compounds can be named as preferred cross-linkable preparations: Diphenyl-methane-4-diisocyanate, hexamethylene-diisocyanate, titanium-acetyl acetonate, aluminum-acetyl acetonate, ferrous-acetyl acetonate, zinc-acetyl acetonate, magnesium-acetyl acetonate, zirconium-acetyl acetonate, 2-ethyl-1,3-hexanediol-titanate, tetra-isooctyl-titanate, tetra-nonyl-titanate, polyfunctional propylene-imine-derivate, ether-derivate from melamine-formaldehyde-resin, high methylated urethane-resin, imine-melamine-resin.

The non-cross linkable contact adhesives may be polymerized preferably from a combination of the following monomers:
2-ethyl-hexyl-acrylate/N-butyl-acrylate/vinylacetate,
2-ethyl-hexyl-acrylate/vinylacetate,
2-ethyl-hexyl-acrylate/N-butyl-acrylatevmnylacetate/allyl-acrylate,
2-ethyl-hexyl-acrylate/N-N-butyl-acrylate/allyl-methacrylate,
2-ethyl-hexyl-acrylate/N-butyl-acrylate/vinylacetate/divinyl-benzol, 2-ethyl-hexyl-acrylate/fumaric acid-diethyl-ester/allyl-acrylate,
2-ethyl-hexyl-acrylate/maleic acid-diethyl-ester/allyl-acrylate,
2-ethyl-hexyl-acrylate/N-butyl-acrylate/acrylamide/vinylacetate/allyl-acrylate,
2-ethyl-hexyl-acrylate/N-butyl-acryate/iso-butyl-acrylate/vinylaetate/allyl-acrylate.

Furthermore a few contact adhesives may be used in the form of an aqueous dispersion (the dispersive type). The use of these dispersive type contact adhesives may bring the advantage that no inflammable or toxic solvents become vaporized during the coating and drying.

Dispersive type contact adhesives may be polymerized preferably from a combination of the following monomers: N-butyl-acrylate/iso-butyl-acrylate/acrylic acid.
2-ethyl-hexyl-acrylate/N-butyl-acrylate/acrylic acid,
2-ethyl-hexyl-acrylate/N-butyl-acrylate/2-hydroxy-ethyl-acrylamide,
2-ethyl-hexyl-acrylate/N-butyl-acrylate/vinylacetate/acrylamide,
2-ethyl-hexyl-acrylate/N-butyl-acrylate/vinylacetate/2-hydroxy-ethyl-acrylate,
2-ethyl-hexyl-acrylate/N-butyl-acrylate/allyl-acrylate-lacrylic acid,
2-ethyl-hexyl-acrylate/N-butyl-acrylate/vinylacetate/divinyl-benzol.

Suitable polyacrylates for use in this invention are cross-linked by multivalent metal ions in order to improve the physical properties of the contact adhesive or in order to adapt it to the specific requirements. The metal ions are normally applied in the form of metal chelate compounds which are soluble in organic solvents. Especially suitable cross-linking agents are aluminum acetate acetonate and titanium acetyl acetonate.

If the contact adhesive used in compliance with this invention is a polyacrylate contact adhesive, the solubility capacity generally depends on the type and the quantity of the free functional groups in the contact adhesive.

The most preferred contact adhesives for use in the device of this invention are the polyacrylates with polar groups, in particular with the free hydroxy groups Examples of such contact adhesives are the polyacrylates for the manufacture of which polar monomers, such as hydroxy-ethyl-acrylate, hydroxy-ethyl-methacrylate, acrylic acid or methacrylic acid are used, for example, in an amount of approximately 1-10% (w/w), especially preferred in a quantity of 3-8% (w/w), notably especially preferred in an amount of 4-6% (w/w). Such contact adhesives are obtainable commercially under the name brand Duro-Tak® (National Starch & Chemicals; Hamburg).

Notably, especially preferred for use in the device of this invention are the contact adhesives of the polyacrylate type, where hydroxy-ethyl-acrylate and/or hydroxyl-ethyl-methacrylate monomers are admixed during polymerization in a quantity of 3-8% (w/w), notably especially preferred in a quantity of 4-6% (w/w).

Such a contact adhesive may be obtained according to the general procedure that is described in U.S. Pat. No. 5,498,418 as follows. The contact adhesive can be obtained through radical polymerization. In a first step a mixture consisting of 21 to 40 percent by weight vinyl acetate, 55-70 percent by weight of an acrylic acid $C_{2-8}$ alkyl ester and 3 to 10 percent by weight of an acrylic acid $C_{2-4}$ hydroxyl acrylic ester is manufactured in an organic solvent with 100 percent by weight monomers in the mixture.

In a second step a conventional cross-linked agent in an organic solvent and—optionally—the active ingredient of the quality required in the transdermal device (patch) for the intended use is admixed, if necessary in an organic solvent.

Finally, in a third step the obtained mixture of the particular acrylate vinyl acetate copolymer is cross-linked in an additional step, conducted through heating and through the removal of the organic solvent or the mixture of solvents used. The active ingredient obtained is "built into" the contact adhesive substance in a special way through the successive and additional cross-linking of the special acrylate vinyl acetate copolymer.

Alternatively the acrylate vinyl acetate copolymer can be polymerized and cross-linked in the absence of the active ingredient. The active ingredient is then only added during the application of the acrylate vinyl acetate copolymer when the patch is manufactured. The acrylate vinyl acetate copolymer has a relative viscosity of 3.0 to 4.2 at 20° C.

Preferably the mixture contains 2-ethylhexyl acrylate and hydroxy ethyl acrylate monomers in addition to vinyl acetate. Preferably the subsequent cross-linking of the special acrylate vinyl acetate copolymers is performed with a titanium acid ester consisting of polybutyl-titanate and/or titanium acetyl acetonate, preferably in a quantity of 0.3 to 3 percent by weight proportional to the weight of the copolymer.

The following steps can cover a process for the manufacture of a TTS in compliance with this invention: As a first step the manufacture of a solution of a copolymer, in which the active ingredient, in the amount required for the intended use of the TTS as well as a conventional cross-linker or a mixture of it, is optionally contained, and whereby the copolymer is obtained through the radical polymerization of a mixture of monomers consisting of 21 to 40 percent by weight vinyl acetate, 55 to 70% by weight of an acrylic acid-$C_{2-8}$ alkyl ester and 1 to 10 percent by weight of an acrylic acid-$C_{2-4}$ hydroxy alkylester, the coating of the above-named solution in the layer thickness required on the protective film of the TTS and the removal of the solvent or the mixing of the solvents by heating, which results in an additional cross-linking of the special acrylate vinyl acetate copolymer.

One form of execution of such a process is characterized by the fact that the acrylate vinyl acetate copolymer, —optionally—the active ingredient, and the cross-linkable agent are dissolved at the start in a solvent, which contains 20 to 40 percent by weight ethanol or an ethanol methanol mixture, with a ratio of solid components consisting of 40 to 60 percent by weight of the mixture of the special acrylate vinyl acetate copolymer of the cross-linkable agent and the active ingredient.

In a different—preferred—form of execution of the invention the active ingredient is only added to the dispersion after cross-linking of the acrylate, which is then spread on the protective film following homogenization.

A particular example of execution for the preparation of such an acrylate-vinyl acetate contact adhesive is published in U.S. Pat. No. 5,498,418, column 2, lines 61 to column 3, line 10. This document is quoted here as a reference.

A particularly preferred contact adhesive for use in this invention are the commercially available contact adhesives Duro-Tak® 387-2287 and Duro-Tak® (3)87-4287 (National Starch & Chemicals; Hamburg). In an especially preferred form of execution of the invention the Duro-Tak contact adhesive is mixed in an appropriate solvent with the desired amount of the active ingredient and the resulting homogenous dispersion spread out in the thickness desired. Finally the solvent or the mixture of solvents is removed at raised temperatures (50-70° C.).

One object of the invention is therefore a device for the transdermal delivery of a compound of Formula I

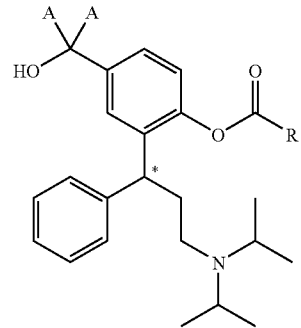

Formula I in which A means hydrogen or deuterium, R stands for a group that is selected from $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" is present in the (R)-configuration,
characterized by the fact that the compound of the general Formula I is present in a polymer layer, preferably in a self adhesive polymer layer (adhesive matrix) where the polymer layer incorporates at least one polymer of the acrylate and/or methacrylate type.

The compound of the Formula I is preferably introduced into the acrylate matrix in the form of the free base, especially preferred in the form of the high purity free base It is especially preferred that the free base be introduced into the inventive acrylate-based matrix, notably especially preferred the high purity base of fesoterodine.

FIG. 3 shows the in-vitro flux rates through mouse skin which were achieved with an acrylate based patch manufactured in a hot melt procedure in which the high purity free base of fesoterodine was introduced into the adhesive matrix.

Auxiliary Agents and Additives

The above described polymer matrices of the transdermal devices containing active ingredient in compliance with the invention may contain other auxiliary agents and additives. Examples are buffers, solutizing agents, crystallation inhibitors, chemical stabilizers, antioxidants, other auxiliary agents for retarding as well as skin penetration enhancers.

Skin penetration enhancers may be used, for example, to enlarge the amount of active ingredient that permeates through the skin or to shrink the application area of the device. Examples of the common penetration enhancers are: Alcohols, in particular short chained alcohols such as ethanol, fatty alcohols, e.g. lauryl alcohol, polyalcohols such as glycerins, amides, e.g. aromatic amides like N,N-diethyl-m-toluamide, amino acids, azones, oils like menthol or peppermint oil; fatty acids and their esters like oleic acids, lauryl acids, isopropyl myristate or glycerol monolaurate; macrocycles such as, for example, cyclopentadecanon; phospholipids such as lecithin for; 2-pyrrolidones as well as sulfoxides such as dimethyl sulfoxide for example.

On account of the good penetration properties of the compounds of the general Formula I, forms of execution of the invention are preferred in which the addition of an enhancer is dispensed with.

A hydrophilic component such as a hydrophilic polymer for example, may be added to the adhesive matrix as another component. These hydrophilic polymers may serve as solubility facilitators or crystallization inhibitors for the compounds of the general Formula I and contribute to a uniform distribution of the active ingredient in the adhesive matrix.

Appropriate hydrophilic polymers for use in the TTS in compliance with the invention may, for example, be chosen from the group of the polysaccharides, substituted polysaccharides, polyethylene oxide, polyvinyl acetate, polyvinyl pyrrolidone (PVP), PVP with appropriate softeners, polyethylene glycols, polypropylene glycols, polyacrylates, copolymers from polyvinyl pyrrolidone and (poly)vinyl acetate, copolymers from ethylene and vinyl acetate as well as polyvinyl alcohols with a suitable softener, for example, glycerin.

Preferred hydrophilic polymers are PVP, polyethylene oxide (PEO), polyvinyl acetate (PVAc) as well as copolymers from PVP and vinyl acetate.

The hydrophilic polymers may be added to the adhesive layer, for example, in a portion of 0.5-40 percent by weight based on the total weight of the adhesive layer. Preferably 2-25 percent by weight, especially preferably 2-15 percent by weight of 2-10 percent by weight hydrophilic polymers are added.

Those hydrophilic polymers which exhibit a dynamic melting viscosity of a maximum 150 Pa's, preferably less than 120 Pa's and especially preferably below 80 Pa's, at temperatures below 170° C. are especially suitable for use in a hot melt procedure. A suitable softener, for example, glycerin, is to be added beforehand if the dynamic viscosity of the hydrophilic polymer is too low at the desired processing temperature.

The addition of the above named hydrophilic polymers may be advantageous, particularly in the case of very hydrophobic adhesive matrices, for example, silicone, polyisobutylene or SXS matrices.

As already described in WO 01/35957, the free bases of the 3,3-diphenylpropylamine-monoester tend towards a drop in concentration, for example, as a result of hydrolysis and interchange esterification. It was then surprisingly determined that the 3,3-diphenylpropylamine-monoesters can be stabilized significantly in matrices with hydrophilic constituent parts.

While, for example, the free base of fesoterodine is decomposed as an oil after storage for 6 months at 5° C. to around 3-4% a drop in concentration cannot be established or can only be established essentially to a lesser extent when fesoterodine is incorporated in matrices, which contain polar components.

Examples for such matrices as these that lead to the stabilization of the monoester of the general Formula I are matrices, for example, that contain polyacrylates, in particular polyacrylates with polar groups, EVA or mixtures of silicone adhesives with hydrophilic polymers, for example, PVP, PVAc or PEO, (Table 4).

TABLE 4

Stabilization of fesoterodine in various matrices during storage

| Matrix | 5° C. Stabilization Factor[1] | 25° C./60% RH Stabilization Factor[1] | Manufacturing Process |
| --- | --- | --- | --- |
| EVA | 7-fold | 4.5-fold | Hot melt |
| Silikon/Cer[3] | — | — | Hot melt |
| Silicone + 2% PVP | 2-fold | 2-fold | Solvent |
| Silikon/Cer[3] + 5% PEO | 3-fold | 2.5-fold | Hot melt |
| Polyacrylate | No decomposition detectable[2] | 13-fold | Solvent |
| PIB | — | — | Solvent |
| SXS | — | 1.1-fold | Hot melt |

[1]The stabilization factor was determined by the division of the average monthly drop in concentration of the fesoterodine base during storage as a raw material (oil) by the average monthly drop in concentration during storage in matrices;
[2]until the end of the period of measurement after 6 months;
[3]Cer = Ceresine As Table 4 shows, the incorporation of fesoterodine in matrices consisting of EVA adhesives; polyacrylate adhesives or mixtures of silicone adhesives with hydrophilic polymers such as PEO or PVP leads to a distinct stabilization of the fesoterodine and is truly independent of the manufacturing process (the hot melt or solvent procedure).

One form of execution of the invention therefore concerns devices in which the compounds of the general Formula I as a free base are subject to a slower drop in concentration than is the case if the free base is stored under identical conditions, not embedded in a polymer as an oil. Preferred forms of execution are those which at 5° C. and/or at 25° C. lead to a 2-, 3-, 7- or 10-fold stabilization of the 3,3-diphenylpropylamine monoester by comparison with storage as a free base.

Especially preferred devices in compliance with the invention are those in which the free base is present in a polymer layer, in which a drop in concentration of a compound of the general Formula I occurs of less than 3%, preferably of less than 2% or 1% in the case of 6-month storage at 4° C. and of less than 10%, preferably less than 5% and especially preferably less than 3% or 1.5% in the case of 3-month storage at 25° C. and 60% atmospheric moisture.

Preferred matrices are those which contain 50-95 percent by weight of an contact adhesive that is chosen from the group of the acrylate adhesives as well as their copolymers, in particular acrylate adhesives with polar groups, for example with free hydroxy groups, EVA-adhesives Silicone adhesives which contain 2-25 percent by weight, preferably 2-10 percent by weight of a hydrophilic polymer, in particular chosen from PEO, PVP or PVAc, SXS- or PIB adhesives which contain 2-25 percent by weight, preferably 2-10 percent by weight of a hydrophilic polymer, Mixtures of hydrophilic contact adhesives (e.g. polar polyacrylates) with hydrophobic contact adhesives (e.g. silicone, SXS or PIB adhesives).

Notably especially preferred contact adhesives for the manufacture of the matrices in compliance with the invention are polyacrylates, in particular those with polar groups. These matrices exhibit both an excellent releasing profile for fesoterodine and outstanding stabilization properties for 3,3-diphenyl propylamine monoesters.

Furthermore, the invention concerns use of the free bases of the Formula I for the manufacture of controlled releasing transdermal forms of drugs.

One aspect of the invention is therefore the use of a compound of Formula I

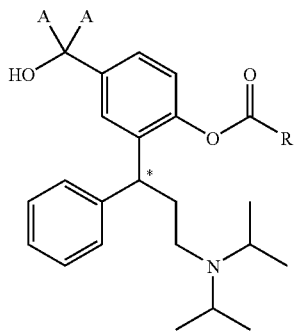

Formula I in the form of the free base in which R stands for $C_{1-6}$-alkyl, $C_{3-10}$-cycloalkyl, substituted or non-substituted phenyl, and in which the C-atom marked with a star "*" is present in the (R)-configuration, for the manufacture of a medicine for transdermal delivery, characterized by the fact that the compound of the general Formula I is added in the form of the free base to a polymer layer, preferably a self-adhesive polymer layer (adhesive matrix).

Preferably the compound of the general Formula I is present as a free base with a degree of purity that is at least 98 percent by weight, preferably at least 99%, especially preferably 99.5% and notably preferably that is at least 99.8%.

In a preferred form of execution the free base of the general Formula I is used for the manufacture of a transdermal medicine which (a) exhibits a surface of a maximum of 40 cm$^2$,
(b) incorporates a self-adhesive polymer layer, which
  (b1) exhibits a weight of 30-300 g/m$^2$,
  (b2) contains 50-95% by weight of a contact adhesive,
  (b3) contains a compound of the general Formula I in a concentration of 5-40 percent by weight based on the total weight of the polymer layer,
(c) delivers said compound of the general Formula I with a steady flux rate of at least 125 μg/hour through the human skin over a time period of at least 24 hours.

A typical and preferred example for such a preferred medicine is a so-called monolithic patch, consisting of an adhesive matrix that contains an active ingredient (1), an inert and impermeable backing for the constituents of the adhesive matrix (2) as well as a protective layer detachable immediately before use (3) (FIG. 4).

In compliance with the invention use of the high purity base of the compound (R)-2-[3-(1,1-diisopropylamino)-1-phenylpropyl]-4-(hydroxymethyl)phenyl isobutyrate (fesoterodine) for the manufacture of the transdermal medicine is especially preferred.

As is evident from FIG. 2 and Table 3, transdermal drugs can be manufactured through the use of the free bases of the general Formula I (in this case: fesoterodine) in compliance with the invention, which when loaded with 15 percent by weight active ingredient and with a surface of 20 cm$^2$, transport the compound of the general Formula I through the human skin at a flux rate of 6-8 mg per day. Consequently, by means of an appropriate variation of the surface from 5-50 cm$^2$, a daily flux of active ingredient between 0.5 and 20 mg over a time period of at least 1 or 2 days is possible in a simple way and without a change to the recipe (Table 3).

By means of a variation in the concentration of the active ingredient and the loading of the device in compliance with the invention, a further adaptation of the burst effect of the active ingredient and/or a monitoring of the duration of the release is also possible.

The devices and drugs respectively are especially suitable for the treatment of incontinence, in particular of urge incontinence, hyperactivity of the detrusor, pollakisuria, nocturia or imperative urinary urgency.

In addition, the invention concerns the manufacture of the devices for transdermal delivery in.

Another object of the invention is a method for the prevention of and/or treatment of incontinence, in particular urge incontinence, hyperactivity of the detrusor, pollakisuria, nocturia or imperative urinary urgency through the administration of a compound of the general Formula I, as described in the above, and/or through the administration of a device in compliance with the invention, containing a compound of the general Formula I, on the skin of a mammal, in particular on the skin of a person, who requires the prevention against or the treatment of the above named diseases.

EXAMPLE EXECUTIONS

1. Manufacture of the High Purity Free Base of Fesoterodine

A. Manufacture of the Fesoterodine Base (B, See FIG. 1, R=i-Pr)

Drops of a solution of 18.6 g isobutyric acid chloride in 250 ml dichloromethane were added in approximately 10 minutes to a solution of 59.8 g (175.1 mol) (R)-2-[3-(diisopropylamino)-1-phenylpropyl]-4-(hydroxymethyl)phenol cooled to −3° C. (A, see FIG. 1) dissolved in 750 ml dichloromethane with agitation and cooling by ice bath. A white substance precipitated after approximately 5 minutes. For this purpose, drops of a solution of 17.7 g triethylamine in 250 ml dichloromethane were added in 5 minutes under agitation and ice bath cooling. The batch was washed once with each of 250 ml water, 250 ml approximate 5% aqueous NaHCO$_3$ solution and 250 ml water. The dichloromethane extract dried over Na$_2$SO$_4$ was evaporated to a low small bulk on a rotary evaporator to constant weight, whereby a sallow, high viscosity oil was left.

Raw yield: 63.7 g (88.5% of the theory).

The purity of B in the HPLC in this example amounted to 94.1%. (Typical range for B: 90.5%-94.4%).

B. Manufacture of the Fumarate Salt (E; FIG. 1; R=i-Pr, X⁻ Hydrogen Fumarate) of Fesoterodine A solution of 41.87 g (102 mmol) (R)-2-(3-diisopropylamino-1-phenylpropyl)-4-hydroxymethylphenyl isobutyric acid ester (B) in 90 ml 2-butanon was laced with fumaric acid (11.81 g, 102 mmol) with heating. Cyclohexane (20-30 ml) was slowly added with agitation until the onset of clouding after dissolving of the acid. The colorless, homogenous batch was initially left for 18 hours at room temperature and then for several more hours at 0° C. The precipitated, colorless crystals were suctioned off, washed with a little cyclohexane/2-butanon (90:10 percent by volume) and vacuum dried at 30° C.

Yield: 44.6 g (83.1% of the theory) of the hydrogen fumarate salt (E) of the (R)-2-(3-diisopropylamino-1-phenylpropyl)-4-hydroxymethylphenyl isobutyric acid ester in the form of colorless small plates.

Melting point 98.8° C., a second crystallization from the same mixture of solvents yielded the product with a melting point of 103° C.

$[\alpha]_D^{20}$=+6.0 (c=1.0, ethanol); −19.3 (c=1.0, acetonitrile).

$^1$H-NMR (CDCl$_3$): among other things 6.84 ppm for CH=from hydrogen fumarate anion.

$^{13}$C-NMR (CDCl$_3$): among other things 135.58 ppm and 170.56 ppm for olefin- and carbonyl carbon from the hydrogen fumarate-anion.

The purity in this example at E (determined with HPLC) amounted to 99.2%.

C. Manufacture of the High Purity Fesoterodine Base (B: FIG. 1, R=i-Pr)

250 g (0.474 mol) crystalline (R)-2-[3-(diisopropylamino)-1-phenylpropyl]-4-(hydroxymethyl)-phenyl-2-methylpropanoate-fumaric acid salt (E) was added to 1 liter water with agitation and heated to 30° C. An almost clear solution was present after approximately 30 minutes. 96.0 g sodium hydrogen carbonate was added with agitation in portions in approximately 10 minutes to the solution cooled to room temperature. 1 liter of dichloromethane was added to the almost clear, colorless solution. After some stirring time at room temperature (strong development of CO$_2$), the dichloromethane phase was cut off and washed successively with each of 5% aqueous sodium hydrogen carbonate solution and 0.2 liters of water. The filtered clear, colorless dichloromethane phase was evaporated on a rotary evaporator to constant weight at a bath temperature of around 40° C., whereby in a final step a diaphragm pump vacuum (ultimate vacuum 5 mbar) was applied. In the course of this (R)-2-(3-diisopropylamino-1-phenylpropyl)-4-hydroxymethylphenyl isobutyric acid ester (B) remained as an almost colorless viscous oil.

Yield: 180.6 g (92.6% of the theory)

$[\alpha]_D^{20}$+5.9 (c=1, ethanol); −6.7 (c=1, acetonitrile)

NMR (CDCl$_3$): 19.01, 19.95, 20.59, 21.12, 34.28, 36.89, 41.88, 42.32, 43.90, 48.78, 64.68, 122.57, 125.59, 126.16, 126.86, 127.96, 128.54, 136.88, 138.82, 143.92, 147.90, 175.69 (ppm).

In this example the purity in the HPLC amounted to 99.0%. Typical purities lie between 98.7% and 99.5%.

$^1$H and $^{13}$C-NMR: No resonance peaks detectable for the hydrogen fumarate anion (compare with E)

The long-term storage is preferably done in the dark under argon at −20° C.

D. Manufacture of the Hydrogen Carbonate Salt (E, FIG. 1: 1: R=i-Pr. X⁻=Hydrogen Carbonate)

fesoterodine (107.7 mg (R)-2-(3-diisopropylamino-1-phenylpropyl)-4-hydroxymethylphenyl isobutyric acid ester, B) is covered with a layer distilled water and stirred at room temperature. After two days of stirring the reaction batch remains unchanged two-phase. No organic material (B or E) could be detected by thin layer chromatography in the aqueous phase at the top (silica gel, solvent system petroleum ether/acetone/triethylamine, 70/20/10 percent by volume).

A slight flow of carbon dioxide gas is fed into the second phase reaction batch at room temperature with agitation. After two days the lower oil phase (fesoterodine) has dissolved totally and clearly in the aqueous phase.

$^{13}$C-NMR-spectrum of the hydrogen carbonate salt of fesoterodine (δ-values):

14.11, 15.36, 15.51, 29.32, 31.09, 38.95, 43.31, 52.38, 60.45, 120.04, 124.07, 124.33, 124.83, 126.12, 131.97, 136.55, 139.06, 144.60, 157.46 ($\overline{HCO_3^-}$), 175.75.

A good conformity results with the $^{13}$C-NMR-spectrum of the hydrogen carbonate salt of fesoterodine, manufactured through the dissolving of the base in 1M aqueous hydrochloric acid.

13.26, 15.32, 15.48, 29.29, 31.06, 38.95, 43.34, 52.42, 60.49, 120.10, 124.18, 124.38, 124.85, 126.13, 131.97, 136.50, 139.02, 144.61, 175.94.

2. Manufacture of the TTS Matrices 2.1. Manufacture of a Silicone Based Matrix in a Hot Melt Procedure 8.5 g of a silicone-based contact adhesive mixture from the silicone adhesive Bio-PSA 7-4300 (Dow Corning, Michigan) was heated to 150° C. with 5 percent by weight ozokerite or ceresine (obtainable from Dow Corning) for around 20 minutes until a homogenous melt came into being.

1.5 g fesoterodine (high purity free base) was added and the mixture kept for a further 5 minutes at 150° C. The mixture was then homogenized by hand and laminated onto a pre-warmed foil (120° C., gap width 250 μm). 5 cm² pieces were cut out for the releasing tests.

2.2. Manufacture of an Acrylate Based Matrix in the Solvent Procedure 1.5 g high purity fesoterodine base was dissolved in dichloromethane and added to a solution of 8.5 g DuroTak® 387-2287 (in ethyl acetate). The resulting mixture was stirred until a homogeneous dispersion was achieved. The dispersion was then spread out on foil and dried (Erichsen 100 μm, 6 mm/sec, drying time: 30 minutes at 50° C.).

2.3. Manufacture of an SXS Based Matrix in a Hot Melt Procedure 100 parts SIS (Styrene Polyisobutylene Styrene, Kraton D1107CU), 150 parts Regalite R 1090, 20 parts Ondina oil and 1 part Irganox were mixed and melted at 140° C. 1.5 g fesoterodine (high purity free base) was added to 8.5 g of each melt and the mixture kept at 140° C. for a further 1-5 minutes. The mixture was then mechanically homogenized and laminated on a pre-warmed sheet (120° C., 250 μm). Pieces of the size desired were cut out.

2.4. Manufacture of an EVA Based Matrix in a Hot Melt Procedure 8.5 g of the EVA hot melt adhesive was heated for around 20 minutes at 160° C. until a homogenous melt was obtained. 1.5 g or more precisely 1.65 g high purity fesoterodine base was added as well and the mixture then homogenized by hand. The mixture was then laminated on a chill roll brought to a specified temperature (120° C.). In each case 5 cm² was cut out (for permeation experiments).

3. Releasing Experiments

3.1. Determination of the Flow of Active Ingredient in the Mouse Skin Model

Belly and back skin in a thickness of approximately 120 to 150 μm was used in a horizontal diffusion cell for the flux measurements through mouse skin. Medium: phosphate buffer solution (0.066 molar) pH 6.2, 32° C.

Release of the active ingredient was determined by HPLC.

3.2. Determination of the Flow of Active Ingredient in the Human Skin Model (a) experimental Design The determination of the fesoterodine flux through human skin was essentially performed as described in H. Tanojo et al, J. Control Rel. 45 (1997) 41-47, where instead of the silicone membrane a dialysis membrane was used [Diachema Dialysemembran, type 10. 14, obtained from the company Dianorm, Munich, Germany, manufactured from neutral cellulose, exclusion size 5000 Da, thickness (dry): 25 μm; pretreatment in accordance with manufacturer information].

Figure 5:
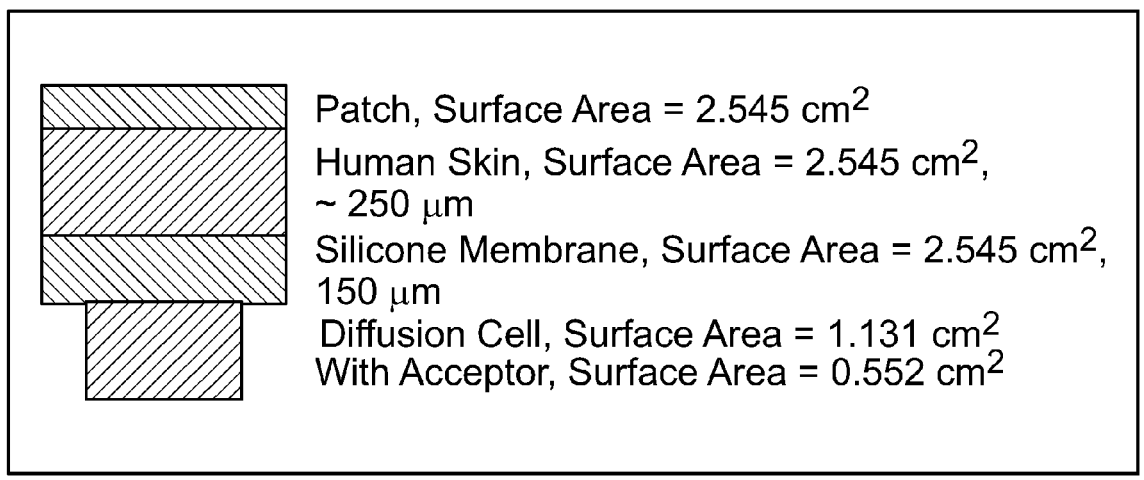
FIG. 5 illustrates the experimental design of the system that was used to determine the flow of active ingredient through human skin.

Human skin in a thickness of approximately 250 μm was obtained from the abdomen. A TTS with a surface of 2.545 cm² was applied on human skin of equal surface size, where the skin on the acceptor site lays on a silicone membrane (FIG. 5). PBS (0.066 molar) was used as the acceptor phase at pH 6.2 and a temperature of 32±0.5° C. The experiments were performed over 72 hours with a 5 ml/hour flux, whereby samples were taken every 3 hours. At the times that the samples are taken, the releasing medium is replaced with fresh medium thermo stated at 32±0.5° C. and the amount of the released fesoterodine measured per HPLC.

The determination of the flux rate Q(t) was done based on the area of the measuring cell (0.552 cm²) in compliance with the formula:

$Q(t)$ μg/cm² = fesoterodine concentration × volume of the acceptor/0.552 cm²

(b) Analytical Chemistry of the Release of the Active Ingredient

The measurement of the active ingredient flux through the skin preparation is done per HPLC (tower Spherisorb 5CN 25 cm) under the following conditions: 4 parts by volume acetonitrile/6 parts by volume $H_2O$/0.1% parts by volume TFA, 35° C., 225 nm, 1 ml flux

4. Analytical Chemistry

Determining the Purity of the Active Ingredient

A HPLC method was used to determine the chemical purity of fesoterodine, which is based on the separation at a stationary reversed phase and used for the gradient elution of a solvent.

Materials (Exemplary Model):

Acetonitrile for the HPLC, methane sulfonic acid (<99%, Fluka), water (purified, HPCL quality), Waters Pump 510, column heater (Waters Column Heater Module, 35° C.), a sampling device (Waters Wisp 717, injection volume 20 μL), UV-detector (Shimatzu SPD 10A). Column (150×3.9 mm, Symmetry Shield RP8, Waters Part No. WAT 200655).

Mobile Phase:

Acetonitrile with 0.05% methane sulfonic acid (v/v, %), Component A

Water with 0.05% methane sulfonic acid (v/v, %), Component B

Gradient program: time (minutes) 0.0 with 15% component A and 85% Component B, after 15 minutes 60% A and 40% B, after 20 minutes 15% A and 85% B. Flux rate: 1.2 ml/minute.

The concentrations of the reference solutions of A, B and C (FIG. 1/4, R=i-Pr) amounted to 10-250 μg/ml. Tailing with peak overlap occurred at the higher concentrations.

Analysis:

The average values of all peak surfaces (triple determinations) were added and compared with 100% for analysis following the 100% method. The areas of the individual peaks were based on this value (as a %). Retention times for A, B and C (minutes): 5.9, 9.0 and 12.6.

5. Analytical Chemistry

Determining the Residual Salt Content

200 MHz or 500 MHz 1H-NMR-spectrums of the free base fesoterodine is absorbed in $CDCl_3$ as the solvent, and characteristic resonance signal groups are integrated electronically, such as:

δ 6.97 ppm (Duplett, aromatic hydrogen, $H^6$, 1H),
δ 4.59 ppm (Singulett, HO—$CH_2$, 2H),
δ 4.10 ppm (Triplett, $H^1$-Propyl, 1H).

The relation to the resonance signal of the anion, for example, Hydrogen fumarate (δ=6.84 ppm, CH—, 2H) results in the proportion of residual salt (as a molecular %).

We claim:

1. A method of treating a mammal suffering from or susceptible to urinary incontinence, the method comprising:
   transdermally administering to the mammal a compound of the following Formula I:

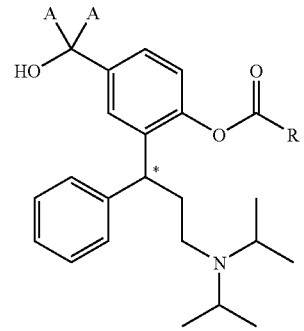

Formula I wherein A is hydrogen or deuterium, R is $C_{1-6}$-alkyl, $C_{3-10}$-cycloalkyl or phenyl, which may each be substituted with $C_{1-3}$-alkoxy, fluorine, chlorine, bromine, iodine, nitro, amino, hydroxyl, oxo, mercapto or deuterium and where the C-atom marked with a star "*" is present in the (R)-configuration, and the compound of Formula I is present as the free base in a polymer matrix.

2. The method of claim 1 wherein the compound of Formula I is added to the polymer matrix in the form of the free base.

3. The method of claim 1 wherein the polymer matrix is self adhesive.

4. The method of claim 1 wherein the polymer matrix is manufactured in a hot melt procedure.

5. The method of claim 1 wherein the polymer matrix is manufactured in a solvent procedure.

6. The method of claim 1 wherein the compound of Formula I is released in a dose of at least 3 mg per day over at least 24 hours at a constant flux rate through human skin.

7. The method of claim 1 wherein the polymer matrix comprises a contact adhesive chosen from among polyacrylates, ethylene vinyl acetates (EVA), polyisobutylenes, silicones or styrene block copolymers (SXS).

8. The method of claim 1 wherein the polymer matrix contains 50-95 percent by weight of a contact adhesive that is selected from the group of:
    (a) polyacrylates
    (b) EVA-contact adhesives,
    (c) silicone adhesives,
    (d) SXS-adhesives,
    (e) PIB-contact adhesives,
    wherein 2-20 percent by weight of a hydrophilic polymer is added to each of the hydrophobic contact adhesives (c), (d) and (e) based on the total weight of the polymer matrix.

9. The method of claim 1 wherein the compound of Formula I is present in a device and the device
    (f) exhibits a surface of a maximum 50 $cm^2$,
    (g) comprises a self-adhesive polymer matrix, which
        (b1) exhibits a weight of 30-300 $g/m^2$,
        (b2) contains 50-95% by weight of a contact adhesive,
        (b3) contains the compound of Formula I in a concentration of 5-40 percent by weight based on the total weight of the polymer matrix and
    (h) delivers the compound of Formula I with a steady flux rate of at least 4 $\mu g/cm^2$/hour through the human skin over a time period of at least 24 hours.

10. The method of claim 1 wherein R is methyl, ethyl, isopropyl, 1-propyl, 1-butyl, 2-butyl, tertiary-butyl, iso-butyl, pentyl or hexyl.

11. The method of claim 1 wherein the compound is (R)-2-[3-(1,1-diisopropylamino)-1-phenylpropyl]-4-(hydroxymethyl)phenyl isobutyrate (fesoterodine).

12. The method of claim 1 wherein the mammal is suffering from or susceptible to urge incontinence.

13. The method of claim 1 wherein the mammal is suffering from or susceptible to hyperactivity of the detrusor.

14. The method of claim 1 wherein the mammal is suffering from or susceptible to abnormally frequent micturation.

15. The method of claim 1 wherein the mammal is suffering from or susceptible to pollakisuria.

16. The method of claim 1 wherein the mammal is suffering from or susceptible to nocturia.

17. The method of claim 1 wherein the mammal is suffering from or susceptible to imperative urinary urgency.

18. The method of claim 1 wherein the mammal is a human.

19. The method of claim 1 wherein the mammal is identified as suffering from urinary incontinence and the compound is administered to the identified mammal.

20. The method of claim 1 wherein the mammal is identified as suffering from urge incontinence, hyperactivity of the detrusor, abnormally frequent micturation, pollakisuria and/or nocturia, and the compounds is administered to the identified mammal.

21. The method of claim 19 wherein the mammal is a human.

22. The method of claim 20 wherein the mammal is a human.

23. The method of any one of claim 1, 11, or 18 wherein the compound can be released through human skin in a dose of 0.5-20 mg per day.

24. The method of claim 23 wherein less than 10% of the compound is present in the salt form.

* * * * *